US012622674B2

(12) United States Patent
Cretu et al.

(10) Patent No.: US 12,622,674 B2
(45) Date of Patent: May 12, 2026

(54) CONTACTLESS CMUT OPERATION

(71) Applicant: THE UNIVERSITY OF BRITISH COLUMBIA, Vancouver (CA)

(72) Inventors: Edmond Cretu, Vancouver (CA);
Carlos D. Gerardo, Vancouver (CA);
Robert Rohling, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 297 days.

(21) Appl. No.: 18/029,819

(22) PCT Filed: Oct. 1, 2021

(86) PCT No.: PCT/CA2021/051378
§ 371 (c)(1),
(2) Date: Mar. 31, 2023

(87) PCT Pub. No.: WO2022/067447
PCT Pub. Date: Apr. 7, 2022

(65) Prior Publication Data
US 2023/0363735 A1     Nov. 16, 2023

Related U.S. Application Data

(60) Provisional application No. 63/086,740, filed on Oct. 2, 2020.

(51) Int. Cl.
A61B 8/00          (2006.01)
B06B 1/02          (2006.01)

(52) U.S. Cl.
CPC .......... *A61B 8/4472* (2013.01); *A61B 8/4236* (2013.01); *A61B 8/4488* (2013.01);
(Continued)

(58) Field of Classification Search
CPC ... A61B 8/4472; A61B 8/4236; A61B 8/4488; A61B 8/56; B06B 1/0207; B06B 2201/51
See application file for complete search history.

(56) References Cited

U.S. PATENT DOCUMENTS 10,509,013 B2     12/2019   Gerardo et al.
10,564,132 B2      2/2020   Gerardo et al.
(Continued)

FOREIGN PATENT DOCUMENTS

CN          206147091 U        5/2017
CN          209625007 U    *  11/2019   ......... G05B 19/0423
(Continued)

OTHER PUBLICATIONS

"David M. Mills, Medical Imaging With Capacitive Micromachined Ultrasound Transducer (CMUT) Arrays, 2004, IEEE Ultrasonics Symposium" (Year: 2004).*
(Continued)

*Primary Examiner* — Abdallah Abulaban
(74) *Attorney, Agent, or Firm* — D'Ambrosio & Menon, PLLC; Usha Menon

(57)          ABSTRACT

Methods, systems, and techniques for the contactless operation of capacitive micromachined ultrasonic transducers (CMUTs) and CMUT arrays. Contactless operations refers to both the contactless transfer of energy and information between the transducer(s) and the controlling subsystem. A system includes a CMUT, a first alternating current voltage source, a first inductor electrically coupled to the first voltage source, and a second inductor electrically coupled to the CMUT. The second inductor is physically decoupled from, and positioned to be wirelessly coupled to, the first inductor. A contactless configuration is useful for a wide range of applications, from wearable transducers to high-end ultrasound imaging systems.

26 Claims, 19 Drawing Sheets

(52) U.S. Cl.
  CPC .............. *A61B 8/56* (2013.01); *B06B 1/0207*
    (2013.01); *B06B 2201/51* (2013.01); *B06B*
    *2201/76* (2013.01)

(56) References Cited

U.S. PATENT DOCUMENTS

| | | | | |
|---|---|---|---|---|
| 10,598,632 | B1 | 3/2020 | Gerardo et al. | |
| 2007/0167133 | A1* | 7/2007 | Tomlinson | G01N 29/07 |
| | | | | 455/39 |
| 2009/0141592 | A1 | 6/2009 | Huang | |
| 2011/0095711 | A1* | 4/2011 | Hsieh | H02M 1/4208 |
| | | | | 318/116 |
| 2012/0326842 | A1* | 12/2012 | Grinberg | G06K 7/10178 |
| | | | | 340/10.1 |
| 2020/0124643 | A1* | 4/2020 | Buhlmann | G01R 19/2513 |
| 2020/0146353 | A1* | 5/2020 | Liu | A24F 40/50 |
| 2020/0254283 | A1* | 8/2020 | Bae | G16H 40/63 |

FOREIGN PATENT DOCUMENTS

| | | | |
|---|---|---|---|
| KR | 10-20190142990 | | 12/2019 |
| KR | 20190142990 | A * | 12/2019 |
| WO | 2017222964 | A1 | 12/2017 |

OTHER PUBLICATIONS

S. D. Senturia, Microsystem design, vol. 3. Kluwer academic publishers Boston, 2001.

D. M. Mills, Medical imaging with capacitive micromachined ultrasound transducer (CMUT) arrays, IEEE Ultrasonics Symposium, 2004, 2004, pp. 384-390 vol. 1.

Sai Chun Tang et al. : "A wireless batteryless deep-seated implantable ultrasonic pulser-receiver powered by magnetic Coupling" IEEE Transactions on Ultrasonics, Ferroelectrics, and Frequency Control, IEEE, U.S.A., vol. 58, No. 6, Jun. 1, 2011, pp. 1211-1221, XP011368805, ISSN: 0885-3010, DOI: 10.1109/TUFFC.2011. 1931.

* cited by examiner

50

$Z_{eq}$

52

$V_{eq}$

53

51

$Z_{eq}$ $I_{eq}$ 52    54

11

105, 106, 107, 108

101, 102, 103, 104

CONTACTLESS CMUT OPERATION

CROSS-REFERENCE TO RELATED APPLICATION

The present disclosure claims priority to U.S. provisional patent application No. 63/086,740, filed on Oct. 2, 2020, and entitled "Contactless polyCMUT operation", the entirety of which is hereby incorporated by reference herein.

BACKGROUND

(a) Field

The invention deals with the contactless operation of ultrasonic transducers and ultrasonic transducer arrays. This method addresses both the contactless transfer of energy and information between the transducer(s) and the controlling subsystem. While there are different types of ultrasound transducers, based on different operating principles—from piezoelectric to Capacitive Micromachined Ultrasonic Transducers (CMUTs), they generally require the application of large voltages (i.e. >50V) for their operation. The novel technology previously invented by the inventors allows the fabrication of polymer-based CMUT (polyC-MUTs) arrays that can be operated at lower voltages, opening the path towards contactless (no wire) operation. The present application describes methods for their contactless operation, useful for a wide range of applications, from wearable transducers to high-end ultrasound imaging systems.

(b) Related Prior Art

Ultrasound transducers have a wide range of applications, from non-destructive testing, consumer electronics (e.g. distance measurement and acoustic interfaces for interaction with objects and position detection, haptic interfaces in smartphones and games, etc.), automotive industry (e.g. potential collision detection) to biomedical imaging systems. They have the large advantage of low cost and non-invasive operation, and thus more than 25% of the clinical medical imaging relies on ultrasound imaging techniques, including the newest features, the 3D and real time 3D imaging. Nevertheless, one of the present limitations of the ultrasonic systems is the physical wire connectivity required between the transducer head and the controlling equipment. This limitation impedes for instance the application of ultrasound transducers as effective wearable body sensors and integrated into more general wearable body sensors networks. The roots of such limitation are to be found in the relative large voltages required by the transducer in order to be effectively operated (in air or in a fluid environment): typically, in ultrasound imaging, pulses with amplitudes around 50V are applied to the transducer in order to generate acoustic pulses that propagate into the medium.

The inventors have previously developed a polymer-based manufacturing technology (U.S. Ser. Nos. 10/509, 013B2, 10/564,132B2 and 10/598,632B1 by Gerardo, Rohling and Cretu) that allows the microfabrication of ultrasonic transducers using polymer membranes, reducing as well the required operating voltages. In this context, at least certain embodiments of the present invention focuses on different techniques that enable a truly contactless/wireless operation of polyCMUTs. While wireless power transfer (WPT) techniques have been applied in the past to various sensor types, there are no wireless, passive ultrasonic transducers.

SUMMARY

According to an embodiment of the invention, there is provided a method for the contactless operation of polyC-MUTs (energy and data transfer) for near-field applications.

According to an embodiment of the invention, there is provided a method for the contactless operation of polyC-MUTs (energy and data transfer) for intermediate-field applications.

According to another embodiment of the invention, there is provided a method for the contactless operation of polyC-MUTs (energy and data transfer) using alternating current (AC) signals.

According to another embodiment of the invention, there is provided a method for the contactless operation of polyC-MUTs (energy and data transfer) using a combination of alternating current (AC) signals and direct current (DC) enabled by an energy storage device (e.g. a battery) located close to the ultrasound transducer.

According to another embodiment of the invention, there is provided a method for the contactless operation of polyC-MUTs (energy and data transfer) using a combination of alternating current (AC) signals and direct current (DC) enabled by two independent electrical transformers.

According to another embodiment of the invention, there is provided a method for the contactless operation of polyC-MUTs (energy and data transfer) using a combination of alternating current (AC) signals and direct current (DC) enabled by an electrical transformer with an internal electrical tap.

At least one embodiment of the invention specifies the method for the contactless (wireless) operation of polyC-MUTs.

According to another embodiment, there is provided a system comprising: a capacitive micromachined ultrasonic transducer (CMUT); a first alternating current voltage source; a first inductor electrically coupled to the first voltage source; and a second inductor electrically coupled to the CMUT, wherein the second inductor is physically electrically decoupled from, and configured to be wirelessly coupled to, the first inductor.

The first inductor and the second inductor may comprise part of a first air-core transformer.

The first inductor and the second inductor may be separated by no more than approximately ten centimeters.

An electrical resonant frequency of the second inductor and the CMUT may be approximately equal to a mechanical resonant frequency of the CMUT, and the first voltage source may be configured to operate at a frequency approximately equal to the electrical or mechanical resonant frequency.

The electrical resonant frequency may be determined as an LC resonant frequency of an inductance of the second inductor and a capacitance between two electrodes of the CMUT.

The system may further comprise: a first antenna electrically coupled to the first inductor; and a second antenna electrically coupled to the second inductor, wherein first and second inductors are wirelessly coupled via the first and second antennas.

The first inductor and the second inductor may be separated by no more than approximately ten meters.

An electrical resonant frequency of the second inductor and the CMUT may be approximately equal to a mechanical resonant frequency of the CMUT, the first voltage source may be configured to operate at a frequency approximately equal to the electrical or mechanical resonant frequency, and an electrical resonant frequency of the first inductor may be approximately equal to the electrical resonant frequency of the second inductor.

The first voltage source may be configured to be operated at a frequency of at least 1 MHz.

The system may further comprise an energy storage device electrically coupled in series with the second inductor and the CMUT.

The system may further comprise: a second alternating current voltage source; a third inductor electrically coupled to the second voltage source; a fourth inductor electrically coupled in series to the second inductor, wherein the fourth inductor is physically decoupled from, and positioned to be wirelessly coupled to, the third inductor; and a rectifier electrically coupled to the fourth inductor and to the CMUT.

The second voltage source may be configured to operate at a frequency outside of a coupling frequency band of the CMUT and higher than that of the first voltage source.

The third and fourth inductors may respectively comprise primary and secondary sides of a second air-core transformer.

The system may further comprise: a third antenna electrically coupled to the third inductor; and a fourth antenna electrically coupled to the fourth inductor, wherein third and fourth inductors are wirelessly coupled via the third and fourth antennas.

The system may further comprise a rectifier tapped along the second inductor and electrically coupled to the CMUT.

The system may further comprise a controller communicatively coupled to the first voltage source, wherein the controller comprises a processor and a memory having stored thereon computer program code executable by the processor and that, when executed by the processor, causes the processor to: operate the first voltage source at a frequency at least a decade above a mechanical resonant frequency of the CMUT; while operating the first voltage source at the frequency at least a decade above the mechanical resonant frequency of the CMUT, measure a reflected impedance of the first inductor; and determine from the reflected impedance a coupling coefficient between the first and second inductors.

The CMUT may be polymer-based.

According to another embodiment, there is provided use of the system of any of the embodiments described above or suitable combinations thereof for obtaining medical information from a patient, wherein the CMUT comprises a polymer-based capacitive micromachined ultrasonic transducer attached to skin of the patient.

According to another embodiment, there is provided use of the system of any of the embodiments described above or suitable combinations thereof for monitoring structural integrity of a pipe, wherein the CMUT comprises a polymer-based capacitive micromachined ultrasonic transducer attached to the pipe.

According to another embodiment, there is provided use of the system of any of the embodiments described above or suitable combinations thereof for obtaining medical information from a patient, wherein the CMUT comprises a polymer-based capacitive micromachined ultrasonic implanted inside the patient.

According to another embodiment, there is provided use of the system of any of the embodiments described above or suitable combinations thereof for monitoring structural integrity of wings of a plane, wherein the CMUT comprises a polymer-based capacitive micromachined ultrasonic transducer attached to the wings.

According to another embodiment, there is provided a method comprising: applying a first alternating current voltage source across a first inductor; wirelessly transferring power from the first alternating current voltage source to a second inductor; and using the wirelessly transferred power to oscillate a capacitive micromachined ultrasonic transducer (CMUT).

The method may further comprise: receiving an echo at the CMUT, wherein the echo results in a current change in the second inductor wirelessly transferring a signal resulting from the current change from the second inductor to the first inductor; and measuring the signal that has been wirelessly transferred.

The first inductor and the second inductor may comprise part of a first air-core transformer.

The first inductor and the second inductor may be separated by no more than approximately ten centimeters.

An electrical resonant frequency of the second inductor and the CMUT may be approximately equal to a mechanical resonant frequency of the CMUT, and the first voltage source may be operated at a frequency approximately equal to the electrical or mechanical resonant frequency.

The electrical resonant frequency may be determined as an LC resonant frequency of an inductance of the second inductor and a capacitance between two electrodes of the CMUT.

The power may be wirelessly transferred using a first antenna electrically coupled to the first inductor and a second antenna electrically coupled to the second inductor.

The first inductor and the second inductor may be separated by no more than approximately ten meters.

An electrical resonant frequency of the second inductor and the CMUT may be approximately equal to a mechanical resonant frequency of the CMUT, the first voltage source may be operated at a frequency approximately equal to the electrical or mechanical resonant frequency, and an electrical resonant frequency of the first inductor may be approximately equal to the electrical resonant frequency of the second inductor.

The first voltage source may be operated at a frequency of at least 1 MHz.

The method may further comprise applying a direct current bias to the CMUT using an energy storage device electrically coupled in series with the secondary side inductor and the CMUT.

The method may further comprise: applying a second alternating current voltage source across a third inductor; wirelessly transferring power from the second alternating current voltage source to a fourth inductor; rectifying the power that is wirelessly transferred from the second alternating current voltage source to the fourth inductor; and using the power that is rectified to apply a direct current bias to the CMUT.

The second voltage source may be operated at a frequency outside of a coupling frequency band of the CMUT and higher than that of the first voltage source.

The third and fourth inductors may respectively comprise primary and secondary sides of a second air-core transformer.

The power from the second alternating current voltage source to the fourth inductor may be wirelessly transferred using a third antenna electrically coupled to the third inductor and a fourth antenna electrically coupled to the fourth inductor.

The method may further comprise: tapping power from the second inductor; rectifying the power tapped from the second inductor; and using the power that is rectified to apply a direct current bias to the CMUT.

The method may further comprise: operating the first voltage source at a frequency at least a decade above a mechanical resonant frequency of the CMUT; while operating the first voltage source at the frequency at least a decade above the mechanical resonant frequency of the CMUT, measuring a reflected impedance of the first inductor; and determining from the reflected impedance a coupling coefficient between the first and second inductors.

The CMUT may be polymer-based.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
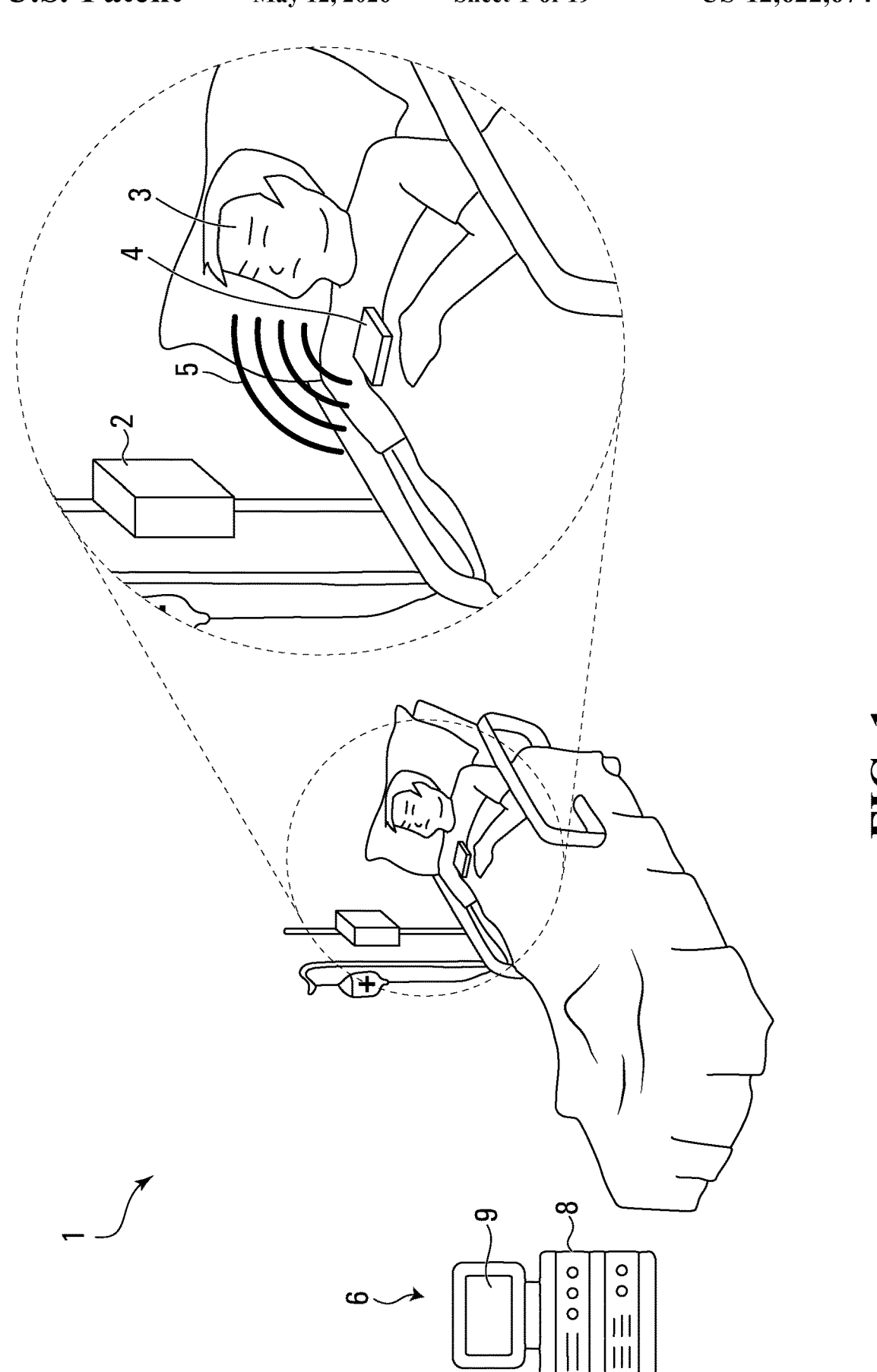
FIG. 1 depicts an example of contactless polyCMUT arrays operating in an intermediate-field scheme where a control unit sends and receives signals from individual transducers placed on patients in hospital beds.

The following terms are defined below.

The term "Capacitive Micromachined Ultrasonic Transducers" (CMUT) is intended to mean an ultrasonic device consisting of an electrically conductive membrane suspended above a cavity. The fabrication materials for CMUTs can be, but are not limited to: silicon, polysilicon, silicon nitride, silicon dioxide.

"The term "Polymer-based Capacitive Micromachined Ultrasonic Transducer" (polyCMUT) is intended to mean a layered ultrasonic device with polymeric membrane containing an embedded upper electrode suspended above a cavity. Examples of a polyCMUT are found in U.S. Ser. Nos. 10/509,013B2, 10/564,132B2 and 10/598,632B1 by Gerardo, Rohling and Cretu, the entireties of all of which are hereby incorporated by reference herein. For clarity, polyCMUTs are considered an example of CMUTs, where polyCMUTs have a top electrode embedded (sandwiched)

between two polymer layers to form the membrane, while CMUTs have the top electrode typically above the membrane.

"Substrate" means an underlying substance or layer upon which the polyCMUTs devices are fabricated. Substrates can comprise a range of metallic (e.g. Aluminum), non-metallic (e.g. ceramics, composite materials), semiconductors (e.g. silicon) and even polymer-based materials such as polyimide. A substrate can also comprise optically transparent or semi-transparent materials such as glass or Indium Tin Oxide (ITO). A substrate can be rigid, semi-rigid or flexible. A substrate can also comprise combinations of the aforementioned options, for example, a piece of glass covered by a layer of Indium Tin Oxide, or a piece of polyimide covered by a metallic layer.

As used herein, "array" is intended to mean a group of polyCMUT elements aligned side by side in a one-dimensional (1D) arrangement, multiple linear arrays located side by side (1.5D) or two-dimensional array (2D array, often called matrix array) of polyCMUT elements in communication with each other and capable of communication (once connected or active) with user interfaces either by wired communication or wireless signals.

As used herein, "contactless" or "wireless" is intended to mean a form of coupling or communication that does not require physical wires. This coupling can be obtained by inductive coupling using a pair of inductors in air or any other media. The coupling can also be obtained by radio frequency (RF) means using antennas or an array of antennas.

As used herein, "field" refers to a space or range within which two or more objects or devices can be reached or can be identified from a particular viewpoint or through a piece of apparatus (such as an antenna).

As used herein, "electrical model" or "model" refers to the representation in the form of electrical components and circuits of systems. These systems can be either in the electrical, the mechanical or acoustic domain and can be represented by standard electrical components.

In this disclosure, the word "comprising" is used in a non-limiting sense to mean that items following the word are included, but items not specifically mentioned are not excluded. It will be understood that in embodiments which comprise or may comprise a specified feature or variable or parameter, alternative embodiments may consist, or consist essentially of such features, or variables or parameters. A reference to an element by the indefinite article "a" does not exclude the possibility that more than one of the elements is present, unless the context clearly requires that there be one and only one of the elements.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.). In this disclosure the singular forms an "an", and "the" include plural referents unless the content clearly dictates otherwise. Thus, for example, reference to a device containing "a system" includes a combination of two or more system.

In this disclosure the term "or" is generally employed in its sense including "and/or" unless the content clearly dictates otherwise.

In this disclosure a first value being "approximately" equivalent to a second value means the first value is within 10% of the second value unless otherwise indicated or the context otherwise requires.

At least some embodiments of the invention addresses various ways for the contactless operation of ultrasonic transducers, for near-field and intermediate-field operation. It solves the problem of the wireless power transfer (to be converted into the acoustic energy necessary for the ultra-sonic interrogation pulses) and of the contactless reading the information provided by the incoming ultrasound signals (from scattered echoes or generated through specific phenomena, like in the case of the photo-acoustic effect). At least some embodiments of the invention addresses several aspects related to the optimum contactless operation in innovative ways:

1. Actuation of the CMUT transducers—to provide electrical voltages that will be efficient in actuation of the ultra-sonic transducers;
2. DC-biasing the CMUT transducers—providing simultaneous DC bias voltage and AC actuation for an optimal CMUT operation;
3. Contactless readout of the acoustic signals received by the CMUT transducer, in order to monitor the acoustic echo signals, or acoustic signals generated by other effects (e.g. photoacoustic effect);
4. Calibration of the received signal, to compensate for the unknown and varying distance between the controller and the CMUT transducer;
5. Individualized selection and addressing of specific CMUT arrays from a present set, or of desired block of CMUT elements within a CMUT array via specific coding and decoding techniques.

At least some embodiments of the invention addresses various modalities for contactless interfacing fully-passive and semi-passive (embedding a DC battery) CMUT arrays with the controller system responsible for its configuration, activation, readout and data processing.

Different techniques can be used depending on the relative distance between the ultrasound transducer and the controller module:

Near-field communication is dedicated to wireless power transfer and communication over short distances (~10 centimeters range), in which an inductive coupling is mostly sufficient.

Intermediate-field communication (centimeter to meters range) is contactless resonant coupling that can extend the communication range between the ultrasonic transducer and the master equipment.

The direct impact of contactless ultrasonic transducers will reflect in a wide range of applications. At the high-end level, the present ultrasound imaging equipment has standardized (costly) cable interfaces for simultaneous operation on 64, 128 or 256 channels. When the number of channels significantly increases, like in the case of 3D imaging, analog multiplexing circuit techniques are used in order to avoid the high increase in the number of connecting wires. The wireless coupling between the transducer head and the data acquisition and processing equipment will enable a much larger configuration flexibility, and an easy, non-obstructed manipulation of the transducer head by the operator.

Referring now to the drawings, and more particularly to FIG. 1, which illustrates a wireless monitoring patient system composed of one monitoring station 1. Each monitoring station has a local controller 2 installed and can accommodate a patient 3 with a wireless polyCMUT system ("patch" ultrasound) 4. In this case, the polyCMUT system 4 monitors the cardiac vital signs of a patient 3. These systems are operating in a near-field or in an intermediate-field scheme. Control signals and (optional) power signals 5 are sent and received wirelessly between the polyCMUT system 4 and the controller unit 2. The entire system is managed by a centralized processing unit 6. The signals coming from the controller unit 2 are received by a connecting cable (not shown) or wirelessly (not shown) and processed in internally by a computer 8. Finally, the information of the monitored patient or patients is displayed on a monitor 9 or sent to a remote monitoring station (not shown). This exemplification highlights some of the benefits of these wireless systems, such as an unobstructed monitoring system (especially useful in intensive care units), a reduced need for electronic and software, the ability to monitor several patients at the same time, among other benefits.

Figure 2:
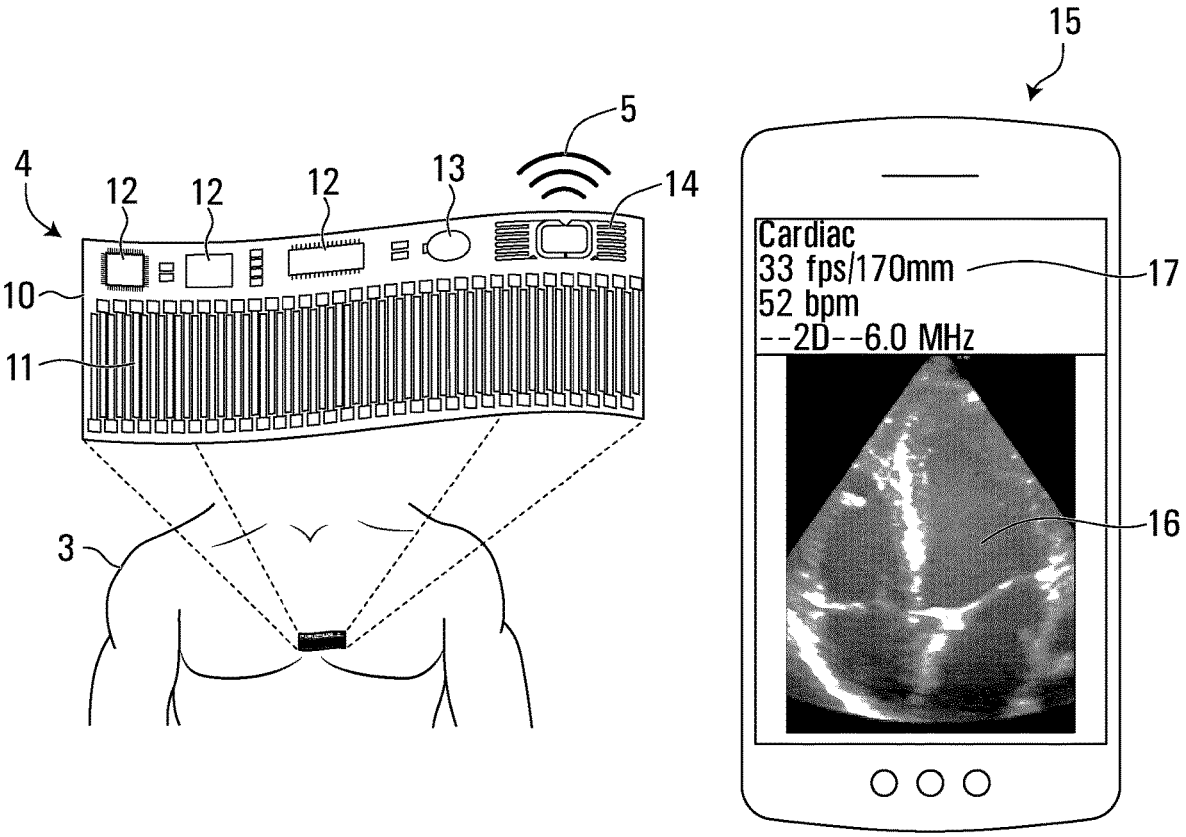
FIG. 2 is an example of a wireless polyCMUT array on a flexible substrate. There is a polyCMUT ultrasound transducer array, controlling electronics, an energy supply system and a wireless antenna. The CMUT array could be coupled wirelessly to a smart phone.

Referring now to FIG. 2, a different category of application relates to wearable ultrasound transducers, attached to the body of patients in the form of small or large patches. The contactless activation and readout of the acoustic echo signals is an essential component of such a system. The "patch" ultrasound 4 can be fabricated on a substrate 10 which can be either rigid, semi-rigid or flexible. A polyCMUT array 11 is fabricated on the substrate 10 and can be a linear array (1D) or a matrix array (2D). Several electronic components 12 are needed for the proper operation of polyCMUTs, such as (but not limited to) beamforming circuits, analog-to-digital converters, microcontrollers, voltage pulsers, multiplexers, etc. An optional energy storage device 13 (such as a battery) can also be part of the system. A wireless antenna 14 is used to send and receive signals to and from a controller (not shown). The ultrasound patch 4 is adhesively fixed on the body 3 for the imaging of a certain area (e.g. heart or lungs), and operated from an electronic device 15 (such as a tablet or smartphone) that can provide the necessary energy for both the transmission of the acoustic signals and the wireless collection of data. The information collected from the polyCMUT is internally processed and displayed either in a display 16 or simply displayed as text information 17.

Near-Field Coupling for Power and Data Transmission

The operation of the CMUT transducer—or more generally of microelectromechanical systems (MEMS) resonator—can be described in terms of the energy flow between the electric and the acoustic domains.

Figure 3A:
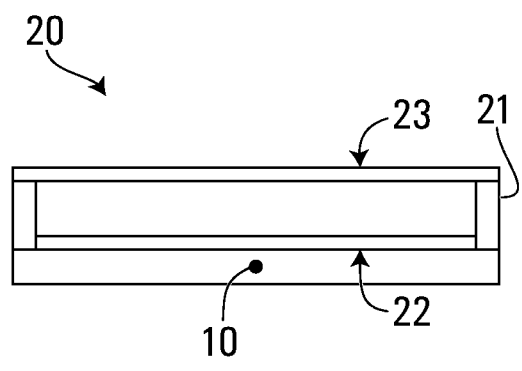
FIG. 3A is a cross sectional view of a standard CMUT cell showing a substrate with a bottom electrode, supporting walls, and a membrane with an electrode.
Figure 3B:
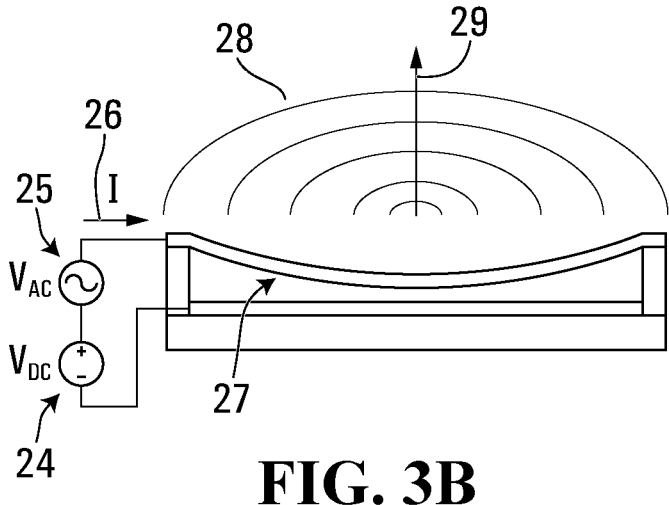
FIG. 3B is a cross sectional view of a standard CMUT operating in transmission (Tx) mode, where AC and DC voltages are combined to deflect the membrane and generate an ultrasound wave.
Figure 3C:
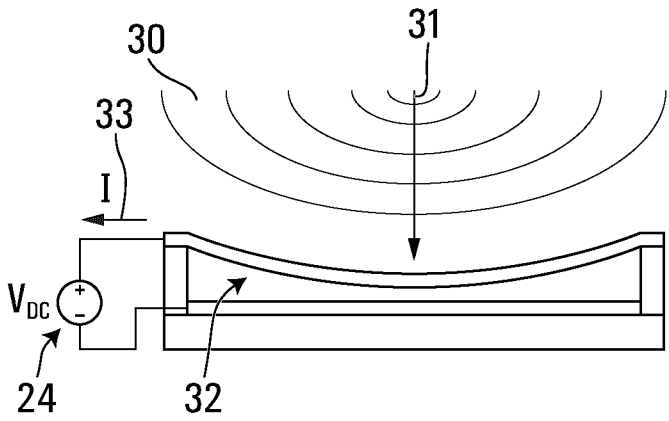
FIG. 3C is a cross sectional view of a standard CMUT operating in receiving (Rx) mode. The membrane is deflected by an incoming ultrasound wave and induces an electrical current on the device while a DC voltage is applied.

The sketch of a basic CMUT transducer cell structure is illustrated in FIG. 3A. The cross-section of a basic CMUT 20 structure shown. It consists of a substrate 10, a fixed electrode 22 integrated on the substrate 10, supporting walls 21 and a second electrode associated with a flexible thin membrane 23. The thin membrane can be itself conductive, or otherwise a conductive electrode is deposited on the top of it or embedded within the membrane (as in U.S. Ser. Nos. 10/509,013B2, 10/564,132B2 and 10/598,632B1, incorporated by reference). FIG. 3B shows the operation of CMUTs in transmit mode (Tx). The bottom 22 and top electrodes 23 are connected to a voltage source comprised of an AC voltage source 25 and an optional DC voltage source 24 which induces an electrical current 26. This electrical current 26 induces an electrostatic force between the electrodes and causes the metalized membrane 23 until a deformation 27 is obtained. The oscillating vibration of the membrane 23 induced by the oscillating current 26 creates ultrasound waves 28 that propagates in a medium (not shown) following a direction 29. FIG. 3C shows a CMUT in receive mode (Rx). The echoes 30 received from reflection surfaces or from scatterers from a certain direction 31 will deform (through the exerted acoustic pressure) the membrane 32. This deformation will change the equivalent electrical capacitance, that can be detected in the electrical domain through the detected current change 33. The operation assumes the application of a DC+AC voltage source—the pre-bias given by the DC voltage source 24 modulates the sensitivity of the transducer and ensures a linearization of its operation, while the AC voltage source 25 actuates the membrane (in packages of pulses or in continuous mode), typically at its mechanical resonance frequency, in order to ensure an optimum electromechanical energy transfer coupling.

Figure 4:
FIG. 4 is the electrical representation of a CMUT device showing the electrical side on the left portion of the circuit and the mechanical side on the right. The mechanical behavior of a CMUT can be modeled as electrical circuit components in this representation.
Figure 4:
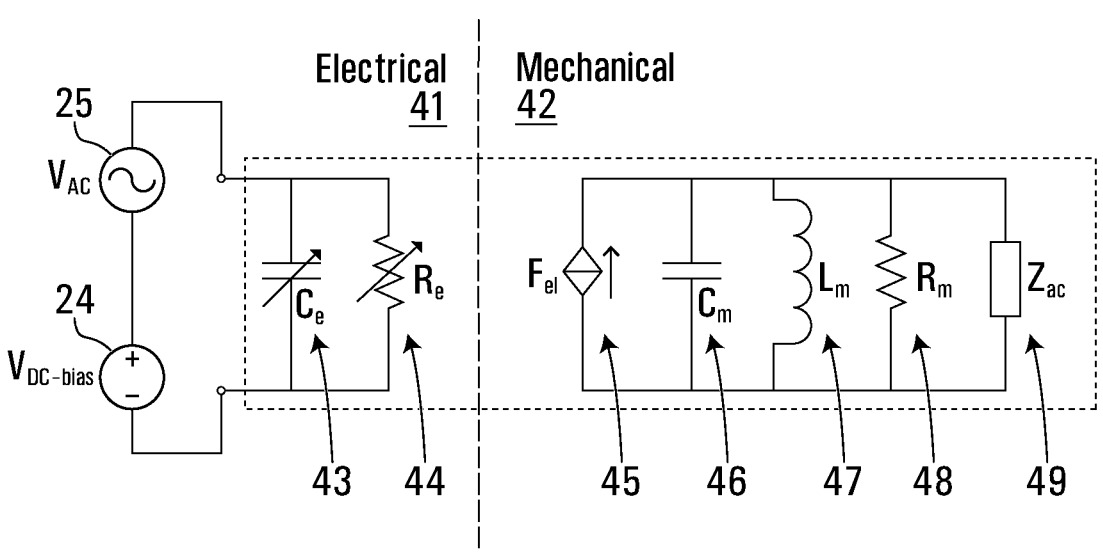

Referring now to FIG. 4, assuming a simplified one degree of freedom model for the displacement of the membrane 40, a reduced order macro-model, based on charge and power conservation principles, useful for explaining the power transfer aspects, is illustrated in FIG. 4, based on a generalized across-through modeling approach [4] that combines the acoustic domain 41 and mechanical domain 42 into a single electrical representation. The equivalent nonlinear capacitor Ce 43 models the electrical capacitance between the two electrodes. The nonlinear electrical resistor Re 44 models the electrical power transfer into the mechanical domain 42. The physical circuit representation in the mechanical domain is based on the power conjugate variables force and velocity, with force as through variable (generalized current) and velocity as across variable (generalized voltage). The electro-mechanical coupling is represented by the nonlinear force controlled source Fe 45; the capacitance Cm 46 represents the effective inertial mass for the corresponding vibration mode, while the inductor Lm 47 models the equivalent spring constant of the CMUT membrane 23. The resistor Rm 48 characterizes the damping of the membrane during its vibration, while the complex impedance Zac 49 represents the equivalent acoustic interaction with the acoustic impedance from the medium. For the back reflected echoes, equivalent acoustic generated forces will be mapped to an external force sources (not shown).

Figures 5A, 5B:
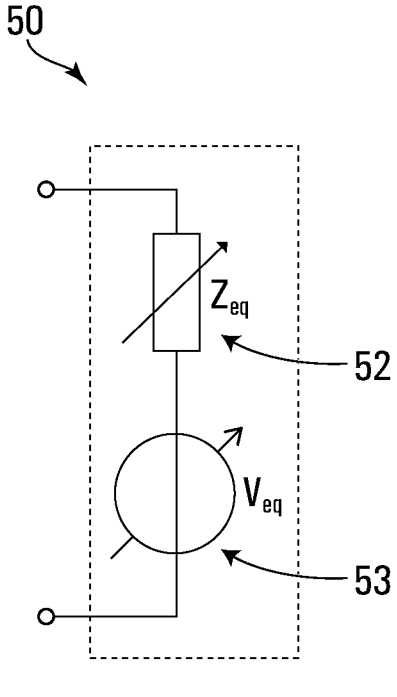
FIG. 5A is a Thevenin equivalent circuit model of a general CMUT device at the electrical port.
FIG. 5B is a Norton equivalent circuit model of a general CMUT device at the electrical port.

Referring now to FIG. 5A, from the physical network representation perspective, the entire dynamic behavior at the electrical port can be characterized by an equivalent (time-varying) Thevenin circuit 50 using an equivalent impedance 52 and an equivalent voltage source 53. Referring now to FIG. 5B. The circuit can also be represented as a Norton equivalent circuit 51 using an equivalent impedance 52 and an equivalent current source 54.

One of the key aspects is that, monitoring only the electrical across/through variables at the electrical port (voltage and current) will provide the necessary information about the relevant processes happening in the acoustic domain. The electrical impedance Zeq 52 will have a capacitive dominated behavior, but with a back reflection of the mechanical resonant behavior that can be detected in the electrical domain. The macromodel circuit 40 is nonlinear and valid for a general large signal operation, being able to predict strongly nonlinear phenomena like electrostatic spring softening and driving the membrane into pull-in or collapse mode (loss of stability border). Nevertheless, for small mechanical vibration amplitudes, it can be linearized around the DC operating point, leading to a linear time invariant equivalent circuit where a gyrator ensures the coupling between the electrical 41 and the mechanical domains 42. The typical energy conversion efficiency for the electro-acoustic coupling is around 85% and depends on the DC operating point determined by the applied DC-bias voltage.

Figure 6A:
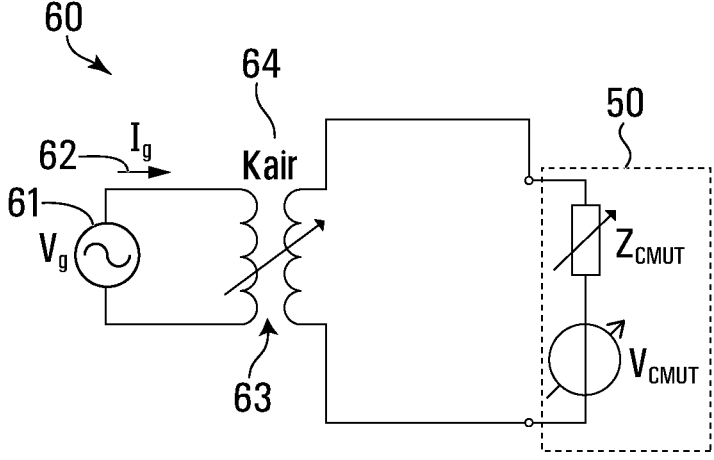
FIG. 6A is an electrical circuit showing an in-air inductive coupling for a near-field contactless CMUT device according to a first embodiment of this document.

A first embodiment of the invention is shown in FIG. 6A, where there is a circuit diagram of a contactless polyCMUT system that operates only in AC 60. The circuit 60 describes the case of the inductive coupling for near-field contactless interface. It has an AC voltage source 61 with a frequency $\omega_1$ (not shown) that supplies an electrical current Ig 62 to an air-core transformer 63 with a coupling coefficient Kair 64. The air-core transformer 63 comprises a first inductor on the transformer's 63 primary side that is inductively coupled to a secondary inductor on the transformer's 63 secondary side; the inductors are physically electrically decoupled from each other. The CMUT element in the form of a Thevenin circuit 50 can be coupled to the electrical domain with the help of two magnetically coupled inductors (transformer 63), one on the master controller side, and the other connected to the CMUT element 50.

In this wireless connection there are two main frequencies. The first one is the electrical LC resonant frequency $\omega_e$ derived from the combination of the inductor on the secondary side of the transformer 63 and the electrical capacitance form the CMUT 43. The second frequency is the mechanical frequency at which the CMUT membrane resonates (its natural vibration frequency in a medium) $\omega_{mech}$ (not shown, but discussed in more detail in respect of FIG. 7 below). It is important to note that a matching between the electrical frequency $\omega_e$ and the mechanical frequency $\omega_{mech}$ is desired for an optimum electromagnetic energy coupling, translating into an increased electromechanical efficiency of the overall system.

The master controller (left portion of circuit 60) provides, in this alternative, through the air-coupled inductors 63, the voltage Vg 61, necessary for the CMUT to operate with optimum efficiency (at its mechanical resonance frequency). In the same time, the controller monitors the value of the current Ig 62, so that it can estimate, at any given moment, the reflected input equivalent circuit (e.g. Thevenin 50 or Norton equivalent 51 port circuit) seen from the primary transformer side, as a readout mechanism. The normal transmit/receive cycle can be similar with the wired operation: a burst of several harmonic periods is transmitted by Vg 61, followed by monitoring the echo responses, reflected in the equivalent Thevenin/Norton parameters.

Figure 6B:
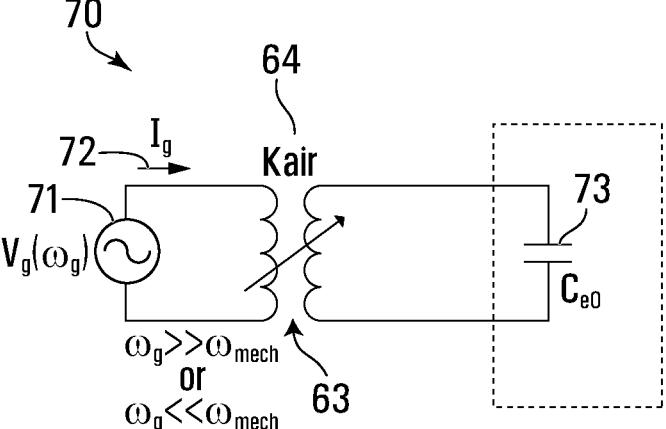
FIG. 6B depicts a calibration setup scheme for contactless CMUT operation. The calibration capacitance is used to determine the transformer ratio in air.

Referring now to FIG. 6B, One of the main challenges with this scheme is that the inductive coupling coefficient will depend on the distance and orientation between the two inductors, making the readout of the echo pulses difficult to calibrate in amplitude. A way of compensating this, with the price of an increased circuit complexity, is to use a calibration circuit 70 with a more complex actuation signal voltage source 71, including a calibration capacitor 73. In normal transmit mode, the voltage source 71 contains a package of several harmonic periods with a frequency tuned for the optimum electromechanical energy transfer (the mechanical resonance frequency). When a calibration is desired, in order to identify the in-air magnetic coupling coefficient Kair 64, a package of harmonic periods will be sent though the current 72, at a frequency much higher than the mechanical resonant frequency (e.g., at least one decade higher), so that the membrane will not vibrate; as a result, a constant and known capacitance value 73 will be reflected into the primary port of the transformer, depending on Kair value. In at least some embodiments, instead of sending a package of harmonic periods, calibration may be performed by operating the voltage source 71 to generate any suitable waveform (e.g., a sinusoid) at a frequency at least one decade higher or at least one decade lower than the mechanical resonant frequency.

The calibration (determination of Kair) is then performed by monitoring the current Ig 72 and indirectly measuring the reflected impedance on the controller side. The inductive coupling method for the transmit and receive operation of CMUT transducers 60 is relatively simple to implement, but it only allows the AC coupling in the circuit presented—it is not possible to apply a direct DC-bias on the CMUT transducer for an optimized operation.

Figure 7:
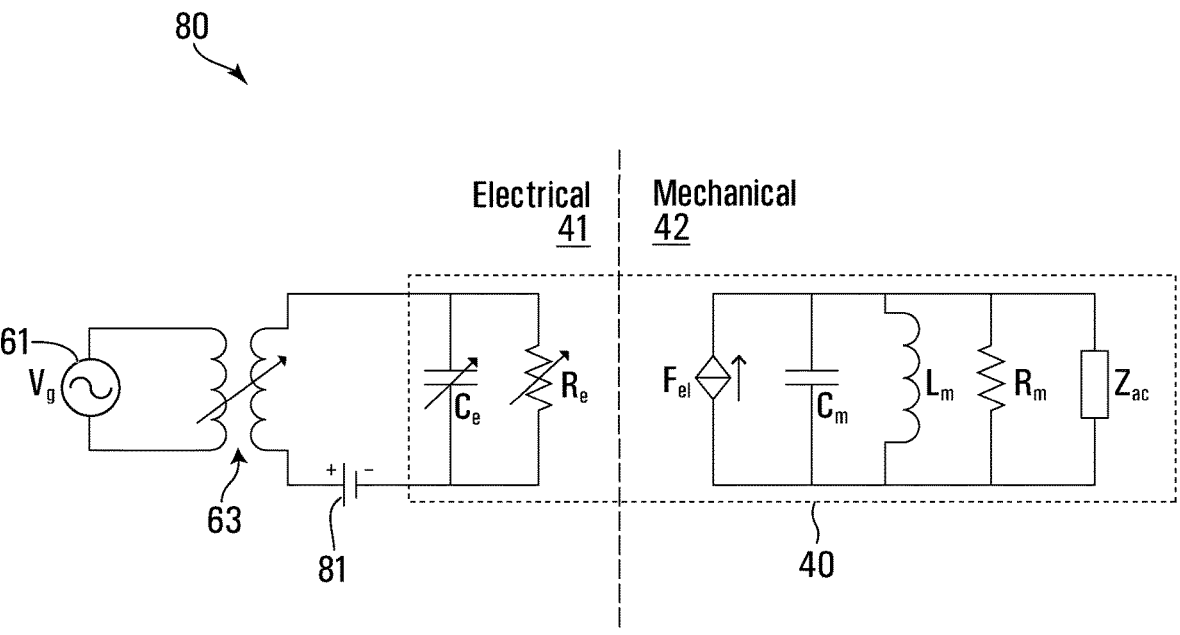
FIG. 7 is an electrical circuit showing a near-field contactless interface for CMUT devices according to a second embodiment of this document. There is an energy storage device (e.g. a battery) that provides a DC voltage for the proper operation of the polyCMUTs.

A second embodiment of the invention is shown in FIG. 7. It is shown a circuit for the contactless operation of CMUTs with DC abilities 80. A separate energy storage device 81 (e.g. DC battery) can be included together with the CMUT element on the secondary side of the circuit, responsible for the DC-bias, but this will only ensure a limited operating time since the energy storage device 81 will discharge over time. In FIG. 7, the mechanical resonant frequency is defined by the resonant frequency of the circuit comprising the combination of Cm, Lm, Rm, and Zac. Practically, Zac may in some situations have no appreciable capacitance (e.g., when the CMUT is emitting an acoustic signal into the air). In other examples, the capacitance of Zac may be relevant (e.g., when the CMUT is emitting an acoustic signal into a liquid).

Figure 8:
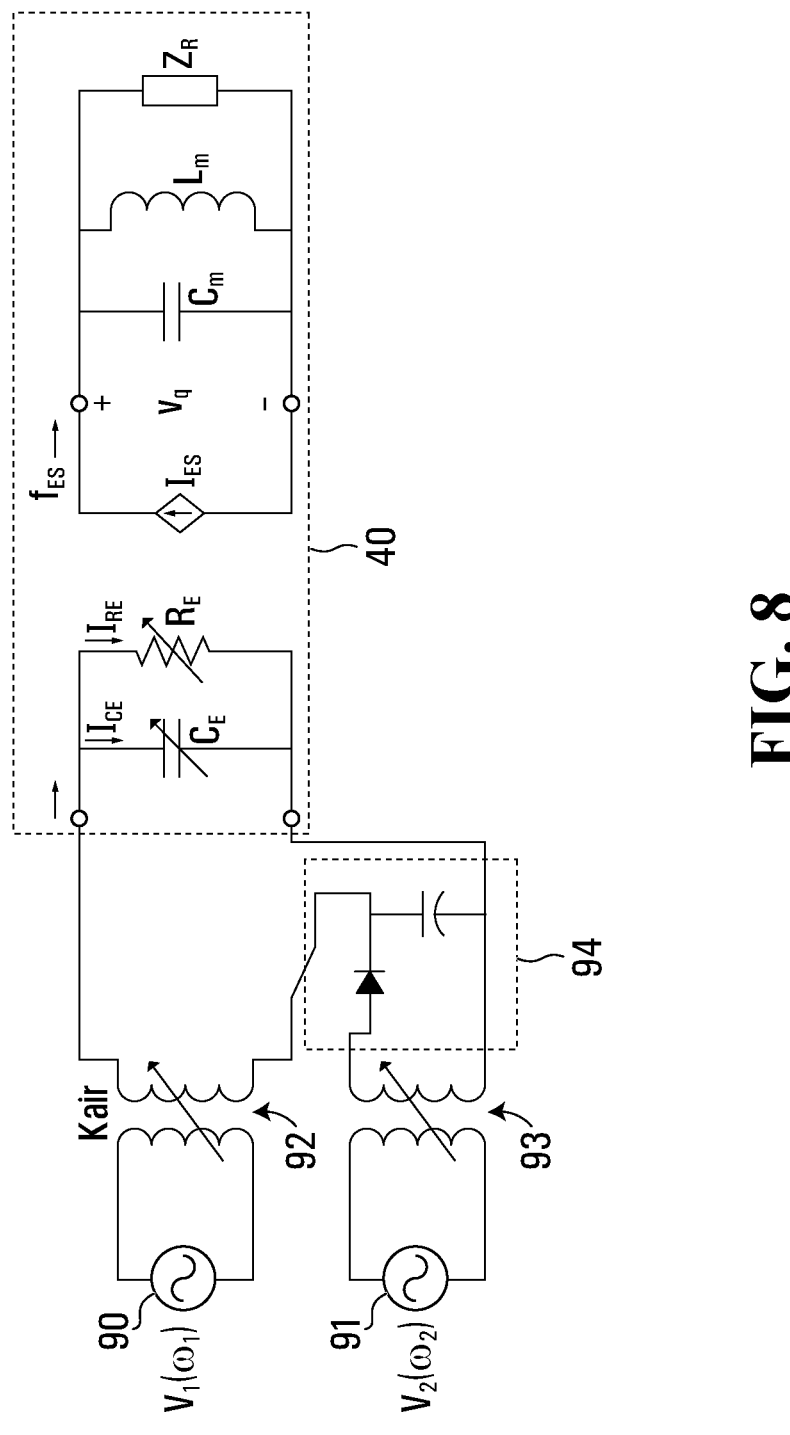
FIG. 8 a depicts an electrical circuit showing a near-field contactless operation of CMUT devices according to a third embodiment. There are two independent transformers that provides AC and DC voltages correspondingly to the electrical portion of the device.

Another embodiment of the invention is shown in FIG. 8. A better alternative is to use the same inductive coupling principle with a circuit that has two separate voltage sources 90 and 91. A first voltage source 90 with a frequency $\omega_1$ will be responsible for the actuation of the CMUT (in the usual packages of sine waves), while a second voltage source 91 with a frequency $\omega_2$ is used to provide the DC-bias voltage. The first voltage source 90 has the frequency $\omega_1$ tuned for the efficient actuation of the CMUT transducer though a first transformer 92, while the second voltage source 91 may have the frequency $\omega_2$ set outside of the CMUT coupling frequency band though the second transformer 93. The first transformer 92 comprises the first and second inductors as described above, while the second transformer 93 comprises a third inductor on its primary side and a fourth inductor on its secondary side. In at least some embodiments, the frequency $\omega_2$ is also higher than the frequency $\omega_1$. The second voltage source 91 will not contribute to the actuation of the CMUT (and therefore will not generate any acoustic signals). A rectification circuit ("rectifier") 94 located on the secondary side of the circuit and interfacing with the second transformer 93 will provide a DC voltage for the operation of CMUTS. This rectifier 94 could be made from passive components only.

Figure 9:
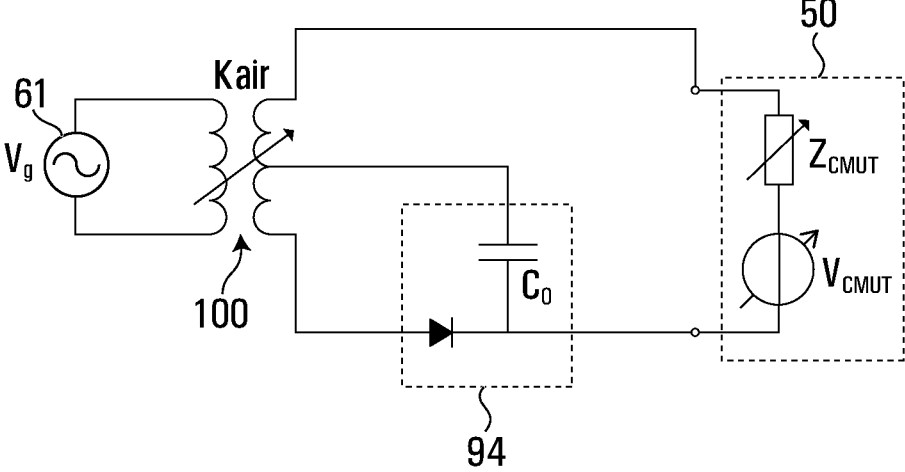
FIG. 9 depicts an electrical circuit showing a near-field contactless operation of CMUT devices according to as separate embodiment. There is a common electrical transformer with an electrical tab on the secondary side that provides AC and DC voltages correspondingly.

Another embodiment of the invention is shown in FIG. 9. A second way of achieving both AC actuation and DC biasing uses a single AC voltage source 61 on the controller side, together with a center tap transformer 100 and a rectifier circuit 94 on the secondary side. The position of the tap in the secondary inductance (secondary side of transformer 100) will dictate the ratio between the DC-bias and the AC actuation voltage. This tap transformer could be fixed or could have a variable tap for an adjustment of the desired DC bias level for the CMUT circuit 50.

Intermediate-Field Coupling for Power and Data Transmission

Figures 10A, 10B:
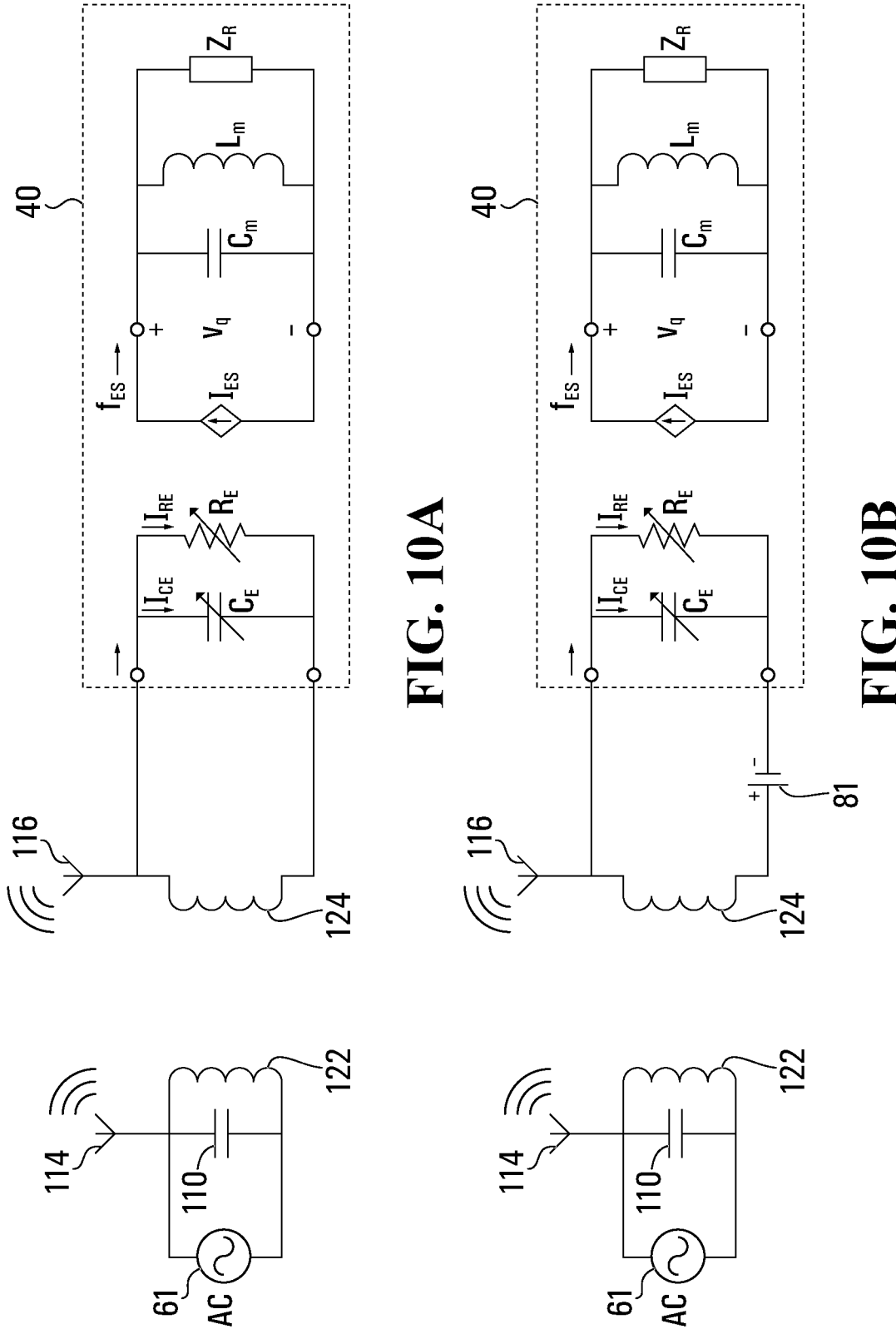
FIG. 10A depicts an electrical circuit showing the contactless operation of CMUTs months using AC voltages only.
FIG. 10B depicts an electrical circuit showing a contactless operation of PolyCMUT where an energy storage device on the secondary side, for example a battery.

Another embodiment of the invention is shown in FIG. 10A. A more efficient power transmission technique, able to deal with intermediate-field power transfer over a couple of meters distance, relies on concentrating the energy transfer in a narrow spectral band through a resonant coupling. In such a case both the side with the voltage source 61 ("master side") and the side with the membrane ("membrane side") comprise matched resonant circuits (e.g., the voltage source 61 operates at the resonant frequency defined by the capacitance 110 and inductance of the first inductor 122, which is equivalent to the electrical resonant frequency on the membrane side of the circuit, which is based at least in part on the inductance of the second inductor 124, and the mechanical resonant frequency of the transducer). FIG. 10A shows a capacitor 110 that affects the resonant frequency on the voltage source side of the circuit, which comprises the first inductor 122. This capacitor 110 may comprise, for example, a tuning capacitor and/or, depending on the frequency used (e.g., when the frequency is at least 100 kHz), the internal (parasitic) capacitance of the first inductor 122. Regardless, the capacitor 110 can be used to define the equivalent electrical inductance-capacitance resonance. On the membrane side of the circuit, the equivalent electrical capacitance of the CMUT will contribute to the electrical resonance. An optimum electroacoustic energy transfer will happen when the electrical resonance frequency $\omega_e$ (not shown) used in the resonant power transfer matches the mechanical resonance $\omega_{mech}$ (not shown) of the vibrating membrane (captured by the circuit 40). A first antenna 114 is electrically coupled to the first inductor 122 and a second antenna 116 is electrically coupled to the second inductor 124 on the membrane side of the circuit. As with the near-field configurations described above, the second inductor 124 is physically electrically decoupled from the first inductor 122 (i.e., it is not connected via a physical conductor such as a wire), and is configured to be wireless coupled to the first inductor 122. In contrast to the near-field configurations above, the second inductor 124 is configured to be wirelessly coupled to the first inductor 122 via the antennas 114, 116. In FIG. 10A and more generally when intermediate-field coupling is dominant, wireless coupling between the inductors 122, 124 occurs via the antennas 114, 116 as opposed to directly between the first and second inductors when those inductors comprise part of the air-core transformer 63 as described in respect of near-field coupling, above.

The increased complexity and the much narrower coupling bandwidth are compensated by larger power transfer distances, in the meters range. The same principles as before apply, FIG. 10A shows the scheme for a simple AC-only actuation and readout scheme.

Another embodiment of the invention is shown in FIG. 10B. It is shown an intermediate-field wireless coupling of CMUTs leveraging the parasitic capacitance represented by capacitor 110. Similar to the case described for FIG. 7, there is an energy storage device 81 on the membrane side that is electrically coupled to the second inductor 124 that provides a DC voltage for the actuation of CMUTs.

Figure 10C:
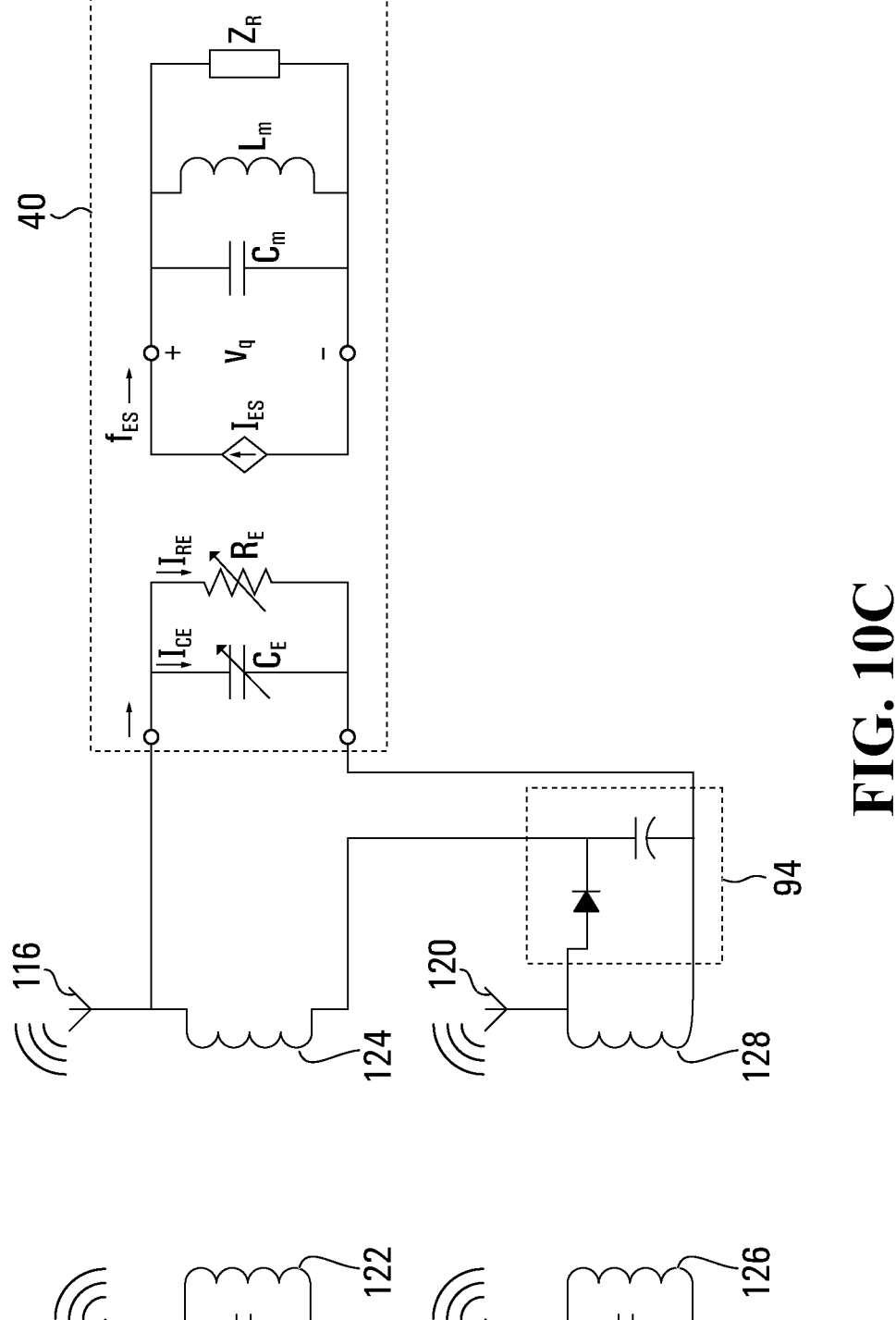
FIG. 10C depicts an electrical circuit showing a contact less operation of CMUT using two independent transformers. An electrical rectifier on the secondary side provides the DC voltage for the operation of CMUT.
Figure 10D:
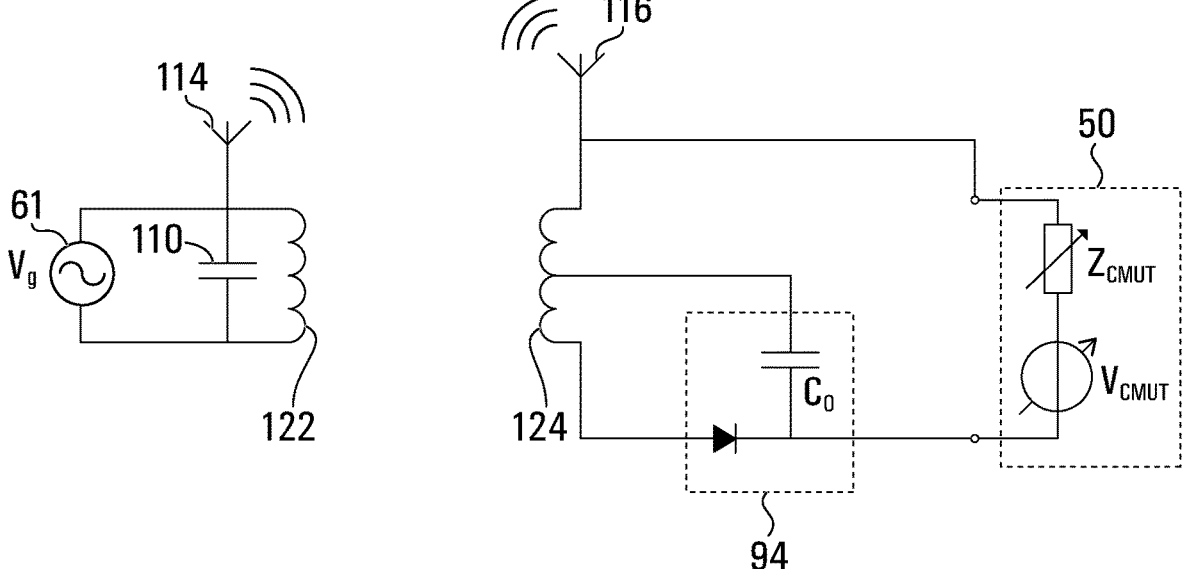
FIG. 10D depicts an electrical circuit showing a contactless operation of CMUT using one single electrical transformer. There is an electrical tap on the secondary side of the transformer and a rectifier that provides DC voltage for the operation of CMUTs.

Other embodiments of the invention are shown in FIG. 10C and in FIG. 10D. FIG. 10C shows a contactless intermediate-field coupling of CMUTs analogous to the near-field configuration of FIG. 8, except the antennas 114, 116 are used to facilitate intermediate-field wireless coupling as opposed to via the air-core transformer 63 of FIG. 8. More particularly, in FIG. 10C two pairs of coils are used: a first pair comprising the first and the second inductors 122, 124 and a second pair comprising the second and the third inductors 126, 128. As in FIG. 10A, the first and the second antennas 114, 116 facilitate intermediate-field wireless coupling between the first and the second inductors 122, 124; analogously, a third antenna 118 electrically coupled to the third inductor 126 and a fourth antenna 120 electrically coupled to the fourth inductor 128 facilitate intermediate-field wireless coupling between the third and the fourth inductors 126, 128. FIG. 10D shows an intermediate-field wireless coupling configuration analogous to the near-field configuration of FIG. 9, with the intermediate-field coupling being facilitated by the antennas 114, 116 as opposed to via the air-core transformer 63 of FIG. 9. In these intermediate-field implementations, capacitors 110, 111 and 112 are used to calibrate the operational transmission frequency of the wireless system, with capacitors 111 and 112 comprising the parasitic capacitances of the inductors 122, 124 when the operating frequency is sufficiently high. In the intermediate-field configurations of FIGS. 10A to 10D, the voltage source 61 may be operated at a frequency sufficiently high, such as at least 1 MHz, to facilitate efficient intermediate-field coupling using the antennas 114, 116, 118, 120.

Experimental Results

Figure 11:
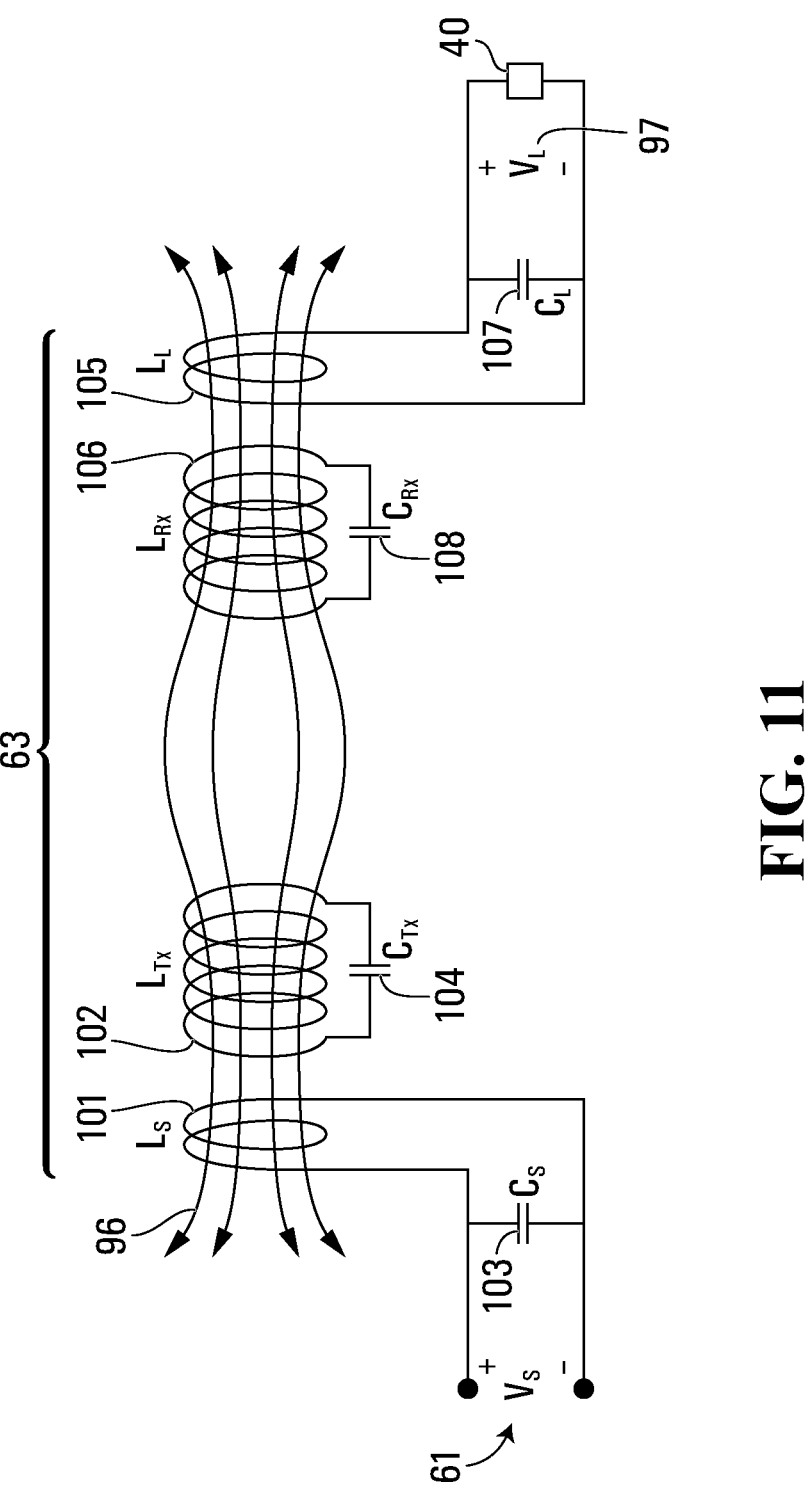
FIG. 11 shows a physical implementation of the circuit shown in FIG. 6A.

Referring now to FIG. 11, there is shown the physical implementation of the circuit shown in FIG. 6A. On the electrical source side (left) it is shown the source inductor 101 and source capacitor 103 magnetically coupled to the transmission inductor 102 and transmission capacitor 104 through the magnetic flux 96. On the load side (right side) it is shown the load inductor 105 and load capacitor 107 magnetically coupled to the receiving inductor 106 and receiving capacitor 108 through the magnetic flux 96. In this case, the group of coils 101, 102, 105 and 106 essentially forms the air-core transformer 63 depicted in FIG. 6A. To maximize the voltage on the receiving side 97, the source inductor 101 and the source capacitor 103 are connected in parallel.

Figure 12:
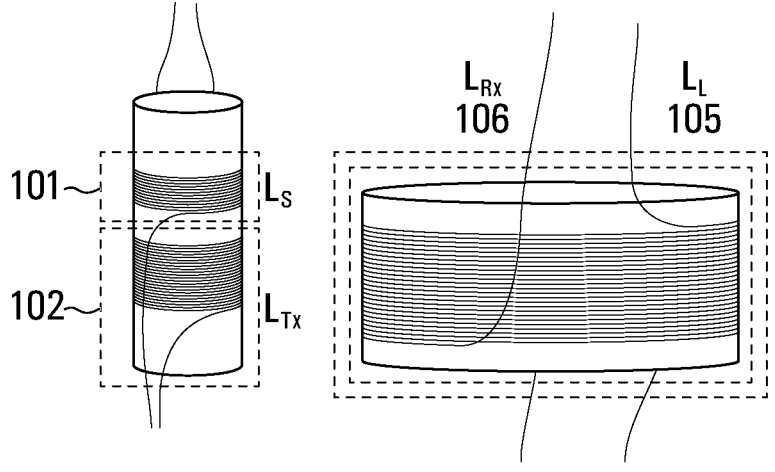
FIG. 12 shows a physical assembly of inductors from FIG. 11.

Referring now to FIG. 12, there is shown the physical assembly of inductors 101, 102, 103 and 104 from FIG. 11. A ferrite core was used on the transmit side to increase the amount of magnetic flux produced, therefore, increasing the operational range (physical separation) between the source inductors (101, 102) and the load inductors (105, 106).

Figure 13:
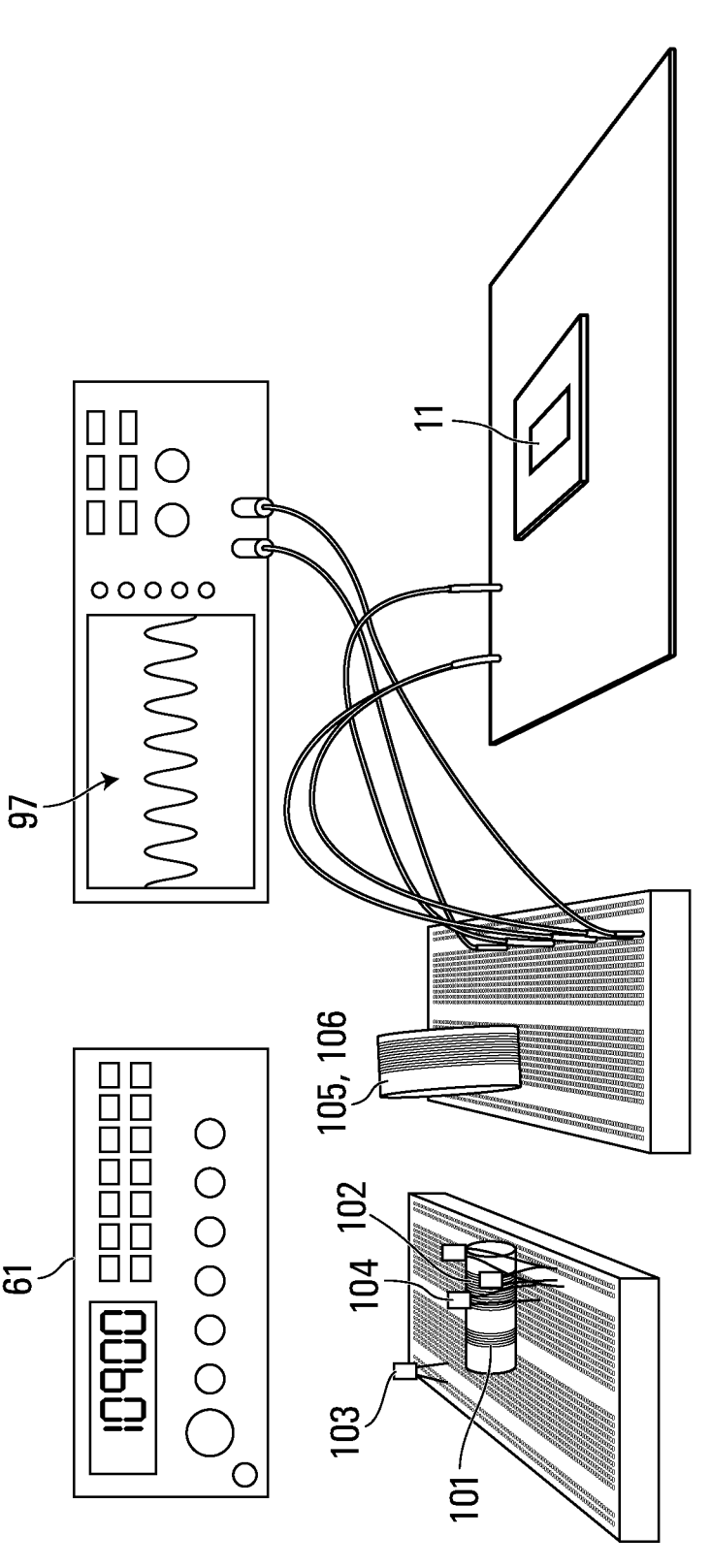
FIG. 13 shows an assembled circuit from FIG. 11.

Referring now to FIG. 13, there is shown an assembled circuit from FIG. 11. A function generator is used as the voltage source 61. The prototyping board on the left is used to assemble the transmit circuit using the source and transmission inductors and capacitors 101, 102, 103, 104. The prototyping board on the right is used to assemble the receiving circuit using the load and receiving inductors and capacitors 105, 106, 107, 108. The receiving circuit is connected to a polyCMUT array 11 using copper wires. The voltage on the receiving side 97 is measured using a laboratory oscilloscope.

Figure 14:
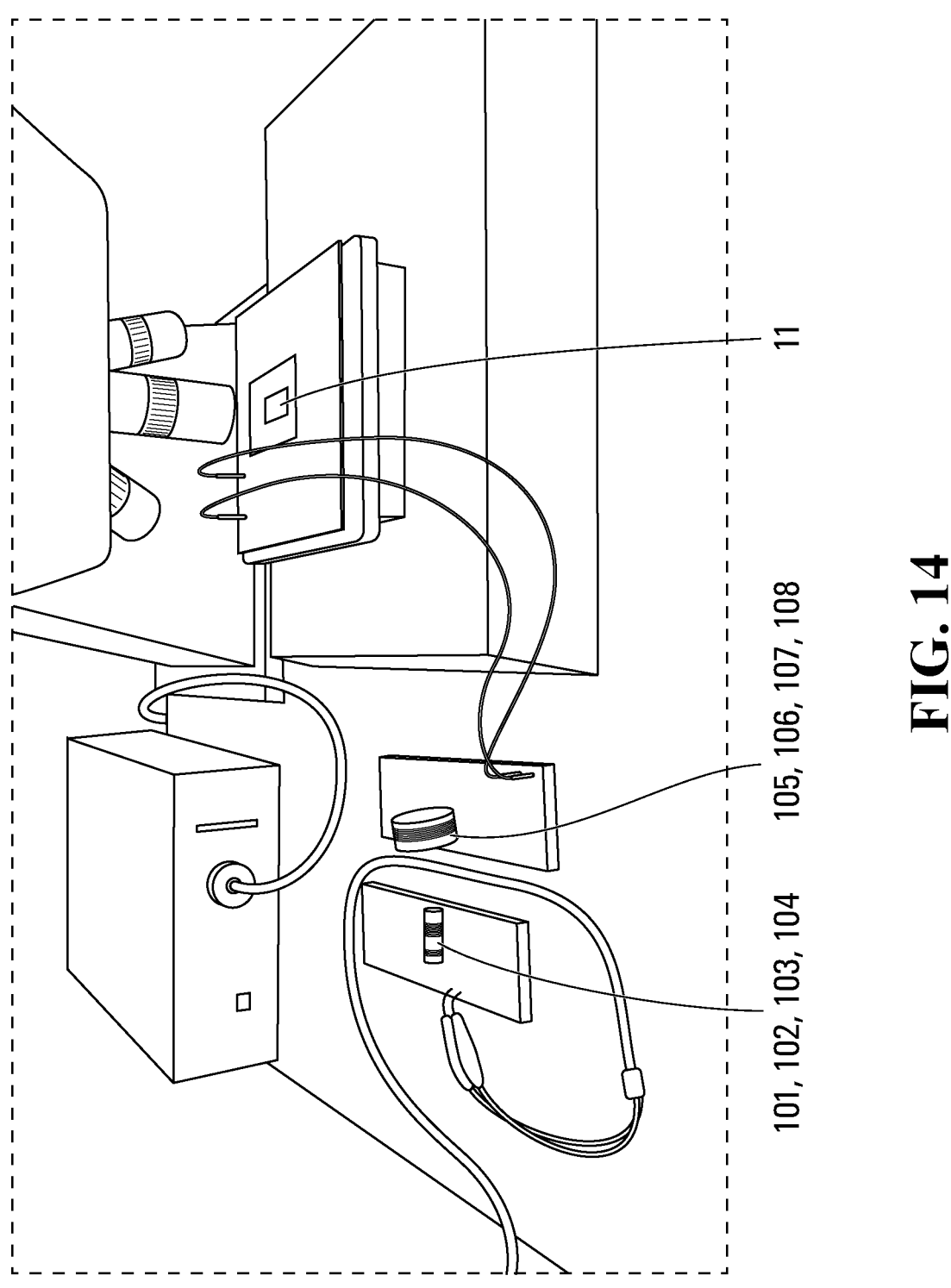
FIG. 14 shows an electromechanical measurement setup for the circuit of FIG. 13.

Referring now to FIG. 14, there is shown the electromechanical measurement setup for the circuit shown in FIG. 13. The transmission inductors and capacitors 101, 102, 103 and 104 are connected to a function generator (not shown) to wirelessly induce a voltage on the receiving inductors and capacitors 105, 106, 107 and 108. The induced voltage on the transmission side 97 powers a polyCMUT linear array 11 located under the microscope lens of a Laser Doppler Vibrometer system MSA-500 (Polytec, CA, USA).

Figure 15:
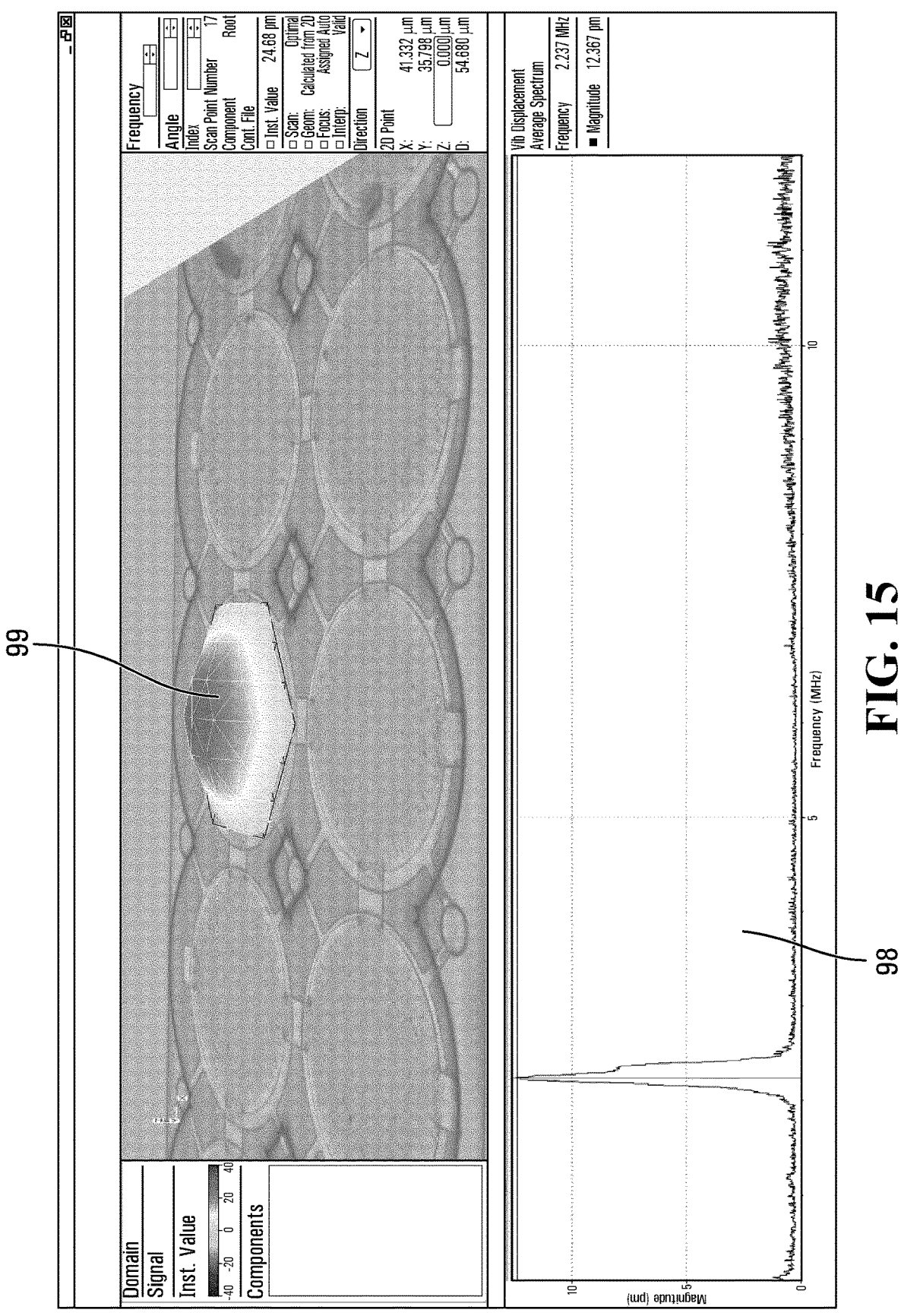
FIG. 15 shows a screenshot of Laser Doppler Vibrometer software generating a deflection shape of an example polyCMUT membrane.

Referring now to FIG. 15, there is shown a screenshot of the Laser Doppler Vibrometer software. It is capable of generating a deflection shape of the polyCMUT membrane 99 automatically using a set of lasers and optical decoders (not shown). The frequency response 98 of the polyCMUT membrane shows a resonant peak at 2.237 MHz when operating in air. For clarity purposes, the polyCMUT membranes from the array 11 are electrostatically actuated by a voltage wirelessly induced by an air-core transformer 63.

Certain embodiments of the present invention will be more readily understood by referring to the following examples which are given to illustrate the invention rather than to limit its scope.

US 12,622,674 B2

15

EXAMPLES

Example 1

In a contactless polyCMUT sensor array mounted on several patients inside a hospital or clinic room, each polyCMUT system obtains vital signs from each patient, for example, blood pressure and ejection fraction of the heart, and optionally images from the inside of the patient. Each of the patients has a polyCMUT-based system associated with his body that communicates wirelessly with a controller and then with a central unit that is capable of controlling several polyCMUT patches at a time. This central unit redirects the gathered information to a local or a remote control station. A technician or a nurse is able to monitor the information from several patients at the same time, and an automatic alert system is part of the monitoring for critical vital signs. The polyCMUT sensor array, controller and central unit keep patients safe, increase efficiency of staff, and reduce the overall electrical, electronic and software requirements for the wireless monitoring of several patients.

Example 2

A set of contactless polyCMUT arrays is permanently installed in pipes to monitor their structural integrity and detect cracks. An operator or a technician can use a wireless controller to "interrogate" the sensor and assess the structural state of the pipe. A wireless antenna could also be coupled to the polyCMUT array that can be then send and receive signals remotely.

Example 3

A miniature wireless polyCMUT sensor is implanted inside the body of a person for a constant real-time monitoring. For example, information on the bladder, heart or other organs are monitored without the person being encumbered by wires. This implanted device is then wirelessly coupled to an electronic readout system (for example a smartphone) using inductive coupling. The communication protocol is initiated manually by the implanted person, or automatically, or even remotely.

Example 4

A wireless polyCMUTs array system is installed (either internally or mounted externally) on the wings of a plane to assess the structural integrity of a wing during flight. The wireless nature of the polyCMUTs ensures a negligible weight is added to the aircraft wings and requires a minimal communication system. The wireless polyCMUT systems can be either interrogated locally from the plane cockpit or remotely from a controlling base station on ground.
Computer Simulations Referring now to FIG. 16, there is shown the schematic diagram for a Simulation Program with Integrated Circuit Emphasis (SPICE) simulation of the circuit shown in FIG. 11. The set of inductors on the primary and secondary side (101, 102, 105, 106) sharing an air-core is implemented as a transformer with multiple windings. The source capacitor 103 and transmission capacitor 104 are connected on the primary side, and the load capacitor 108 and receiving capacitor 108 are connected on the secondary side. Using this configuration, the source voltage 61 is used to wirelessly induce a voltage 97 on the secondary side that drives the reduced order macro-model of a CMUT element 40, where Vq represents the velocity of the vibrating membrane.

Figure 16:
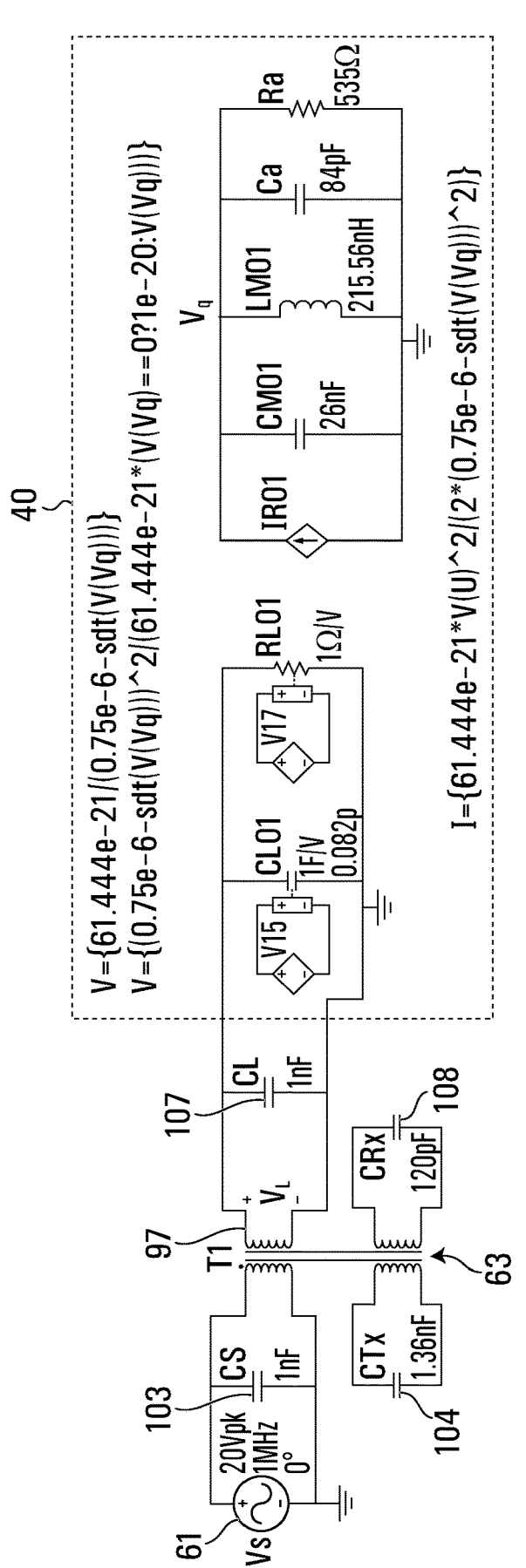
FIG. 16 shows a schematic diagram for a SPICE simulation of the circuit of FIG. 11.
Figure 17:
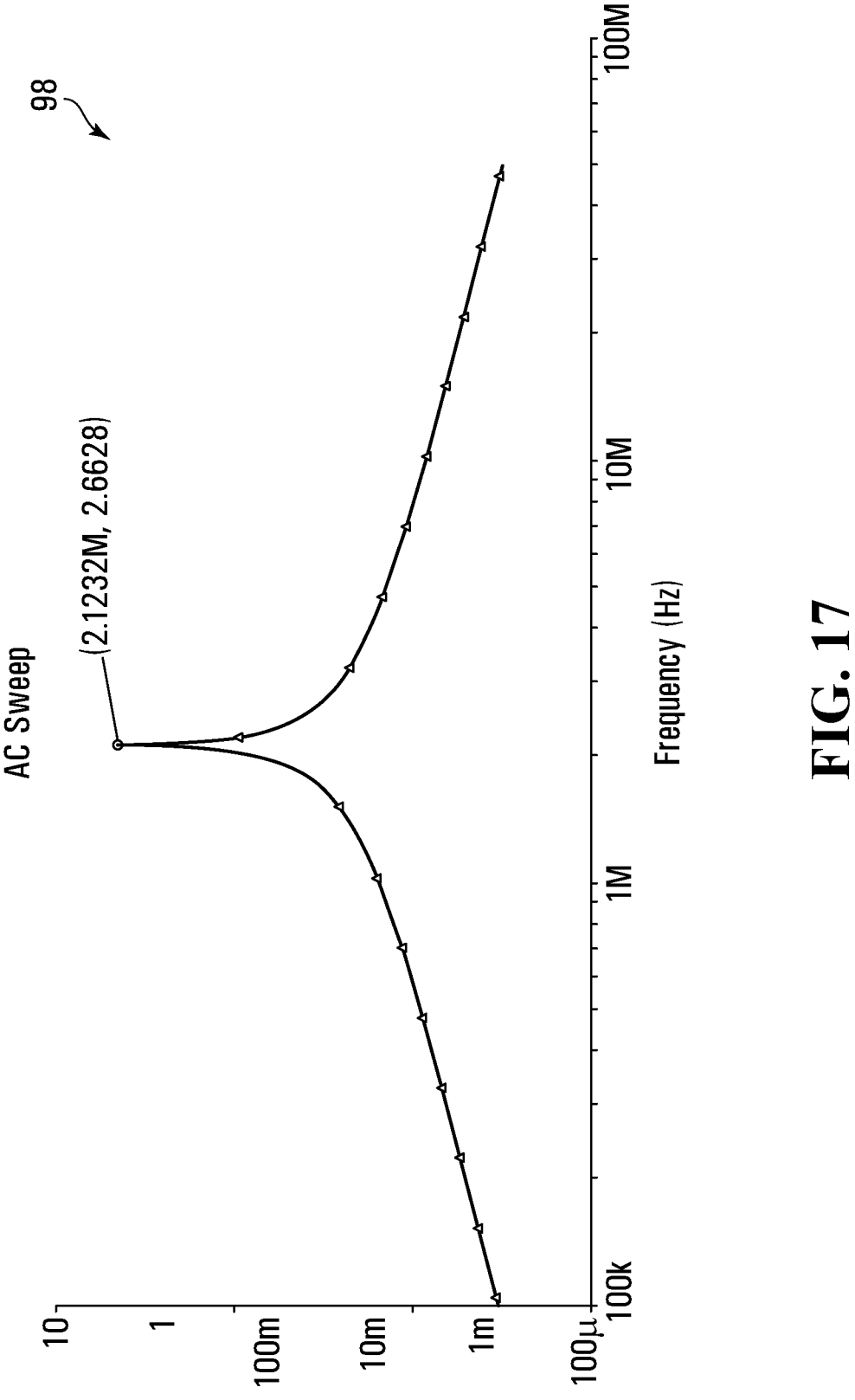
FIG. 17 shows a frequency response from the circuit of FIG. 16.

Referring now to FIG. 17, there is shown the frequency response from the circuit in FIG. 16. The SPICE modeler Multisim™ (National Instruments, Texas, USA) was used for this analysis. A frequency sweep of the input voltage induces a displacement of the membrane measured though the voltage Vq (from FIG. 16). The resonant peak is located at 2.12 MHz and matches closely to the frequency response 98 obtained experimentally from FIG. 18.

It is contemplated that any part of any aspect or embodiment discussed in this specification can be implemented or combined with any part of any other aspect or embodiment discussed in this specification.

While preferred embodiments have been described above and illustrated in the accompanying drawings, it will be evident to those skilled in the art that modifications may be made without departing from this disclosure. Such modifications are considered as possible variants comprised in the scope of the disclosure.

REFERENCES

[1] C. D. Gerardo, R. Rohling, and E. Cretu, "Method for fabricating a layered structure using wafer bonding," U.S. Ser. No. 10/509,013B2, Dec. 17, 2019.
[2] C. D. Gerardo, R. Rohling, and E. Cretu, "Method for fabricating a layered structure using surface micromachining," U.S. Ser. No. 10/564,132B2, Feb. 18, 2020.
[3] C. D. Gerardo, R. Rohling, and E. Cretu, "Layered structure and method for fabricating same," U.S. Ser. No. 10/598,632B1, Mar. 24, 2020.
[4] S. D. Senturia, Microsystem design, vol. 3. Kluwer academic publishers Boston, 2001.

The invention claimed is:
1. A system comprising:
(a) a capacitive micromachined ultrasonic transducer (CMUT);
(b) a first alternating current voltage source;
(c) a first inductor electrically coupled to the first voltage source; and
(d) a second inductor electrically coupled to the CMUT, wherein the second inductor is physically electrically decoupled from, and configured to be wirelessly coupled to, the first inductor;
(e) a first antenna electrically coupled to the first inductor; and
(f) a second antenna electrically coupled to the second inductor, wherein first and second inductors are wireless coupled via the first and second antennas,
wherein an electrical resonant frequency of the second inductor and the CMUT is approximately equal to a mechanical resonant frequency of the CMUT, wherein the first voltage source is configured to operate at a frequency approximately equal to the electrical or mechanical resonant frequency, and wherein an electrical resonant frequency of the first inductor is approximately equal to the electrical resonant frequency of the second inductor.
2. The system of claim 1, wherein the first inductor and the second inductor are separated by no more than approximately ten meters.
3. The system of 1, wherein the first voltage source is configured to be operated at a frequency of at least 1 MHz.
4. The system of claim 1, further comprising an energy storage device electrically coupled in series with the second inductor and the CMUT.

5. The system of claim 1, further comprising:

(a) a second alternating current voltage source;

(b) a third inductor electrically coupled to the second voltage source;

(c) a fourth inductor electrically coupled in series to the second inductor, wherein the fourth inductor is physically decoupled from, and positioned to be wirelessly coupled to, the third inductor; and (d) a rectifier electrically coupled to the fourth inductor and to the CMUT.

6. The system of claim 5, wherein the second voltage source is configured to operate at a frequency outside of a coupling frequency band of the CMUT and higher than that of the first voltage source.

7. The system of claim 5, wherein the third and fourth inductors respectively comprise primary and secondary sides of a second air-core transformer.

8. The system of claim 5, further comprising:

(a) a third antenna electrically coupled to the third inductor; and (b) a fourth antenna electrically coupled to the fourth inductor, wherein third and fourth inductors are wirelessly coupled via the third and fourth antennas.

9. The system of claim 1, further comprising a rectifier tapped along the second inductor and electrically coupled to the CMUT.

10. The system of claim 1, wherein the CMUT is polymer-based.

11. Use of the system of claim 1 for obtaining medical information from a patient, wherein the CMUT comprises a polymer-based capacitive micromachined ultrasonic transducer attached to skin of the patient.

12. Use of the system of claim 1 for monitoring structural integrity of a pipe, wherein the CMUT comprises a polymer-based capacitive micromachined ultrasonic transducer attached to the pipe.

13. Use of the system of claim 1 for obtaining medical information from a patient, wherein the CMUT comprises a polymer-based capacitive micromachined ultrasonic transducer implanted inside the patient.

14. Use of the system of claim 1 for monitoring structural integrity of wings of a plane, wherein the CMUT comprises a polymer-based capacitive micromachined ultrasonic transducer attached to the wings.

15. A method comprising:

(a) applying a first alternating current voltage source across a first inductor;

(b) wirelessly transferring power from the first alternating current voltage source to a second inductor; and (c) using the wirelessly transferred power to oscillate a capacitive micromachined ultrasonic transducer (CMUT);

(d) receiving an echo at the CMUT, wherein the echo results in a current change in the second inductor;

(e) wirelessly transferring a signal resulting from the current change from the second inductor to the first inductor; and (f) measuring the signal that has been wirelessly transferred, wherein the power is wirelessly transferred using a first antenna electrically coupled to the first inductor and a second antenna electrically coupled to the second inductor, wherein an electrical resonant frequency of the second inductor and the CMUT is approximately equal to a mechanical resonant frequency of the CMUT, wherein the first voltage source is operated at a frequency approximately equal to the electrical or mechanical resonant frequency, and wherein an electrical resonant frequency of the first inductor is approximately equal to the electrical resonant frequency of the second inductor.

16. The method of claim 15, wherein the first inductor and the second inductor are separated by no more than approximately ten meters.

17. The method of claim 15, wherein the first voltage source is operated at a frequency of at least 1 MHz.

18. The method of claim 15, further comprising applying a direct current bias to the CMUT using an energy storage device electrically coupled in series with the secondary side inductor and the CMUT.

19. The method of claim 15, further comprising:

(a) applying a second alternating current voltage source across a third inductor;

(b) wirelessly transferring power from the second alternating current voltage source to a fourth inductor;

(c) rectifying the power that is wirelessly transferred from the second alternating current voltage source to the fourth inductor; and (d) using the power that is rectified to apply a direct current bias to the CMUT.

20. The method of claim 19, wherein the second voltage source is operated at a frequency outside of a coupling frequency band of the CMUT and higher than that of the first voltage source.

21. The method of claim 19, wherein the third and fourth inductors respectively comprise primary and secondary sides of a second air-core transformer.

22. The method of claim 19, wherein the power from the second alternating current voltage source to the fourth inductor is wirelessly transferred using a third antenna electrically coupled to the third inductor and a fourth antenna electrically coupled to the fourth inductor.

23. The method of claim 15, further comprising:

(a) tapping power from the second inductor;

(b) rectifying the power tapped from the second inductor; and (c) using the power that is rectified to apply a direct current bias to the CMUT.

24. The method of claim 15, wherein the CMUT is polymer-based.

25. A system comprising:

(a) a capacitive micromachined ultrasonic transducer (CMUT);

(b) a first alternating current voltage source;

(c) a first inductor electrically coupled to the first voltage source; and (d) a second inductor electrically coupled to the CMUT, wherein the second inductor is physically electrically decoupled from, and configured to be wirelessly coupled to, the first inductor;

(e) a first antenna electrically coupled to the first inductor; and (f) a second antenna electrically coupled to the second inductor, wherein first and second inductors are wireless coupled via the first and second antennas;

(g) a controller communicatively coupled to the first voltage source, wherein the controller comprises a processor and a memory having stored thereon computer program code executable by the processor and that, when executed by the processor, causes the processor to:

(i) operate the first voltage source at a frequency at least a decade above a mechanical resonant frequency of the CMUT;

(ii) while operating the first voltage source at the frequency at least a decade above the mechanical resonant frequency of the CMUT, measure a reflected impedance of the first inductor; and (iii) determine from the reflected impedance a coupling coefficient between the first and second inductors.

26. A method comprising:

(a) applying a first alternating current voltage source across a first inductor;

(b) wirelessly transferring power from the first alternating current voltage source to a second inductor; and (c) using the wirelessly transferred power to oscillate a capacitive micromachined ultrasonic transducer (CMUT);

(d) receiving an echo at the CMUT, wherein the echo results in a current change in the second inductor;

(e) wirelessly transferring a signal resulting from the current change from the second inductor to the first inductor;

(f) measuring the signal that has been wirelessly transferred, wherein the power is wirelessly transferred using a first antenna electrically coupled to the first inductor and a second antenna electrically coupled to the second inductor;

(g) operating the first voltage source at a frequency at least a decade above a mechanical resonant frequency of the CMUT;

(h) while operating the first voltage source at the frequency at least a decade above the mechanical resonant frequency of the CMUT, measuring a reflected impedance of the first inductor; and (i) determining from the reflected impedance a coupling coefficient between the first and second inductors.

\* \* \* \* \*